United States Patent [19]
Goto et al.

[11] Patent Number: 5,747,420
[45] Date of Patent: May 5, 1998

[54] TETRAZOLINONES

[75] Inventors: Toshio Goto, Shimotsgua-gun; Seishi Ito; Kazuhiro Ukawa, both of Oyama; Yukiyoshi Watanabe, Saitama; Shin-ichi Narabu, Ibaraki; Akihiko Yanagi, Tochigi, all of Japan

[73] Assignee: Nihon Bayer Agrochem K.K., Tokyo, Japan

[21] Appl. No.: 552,900

[22] Filed: Nov. 3, 1995

[30] Foreign Application Priority Data

Nov. 11, 1994 [JP] Japan ................... 6-301604

[51] Int. Cl.$^6$ ............... C07D 257/06; C07D 295/104; C07D 403/06; C07D 413/06
[52] U.S. Cl. ............ 504/209; 504/226; 504/230; 504/249; 504/247; 504/261; 504/284; 504/287; 544/111; 546/168; 546/176; 546/210; 548/251; 548/253; 548/254; 548/503; 548/510; 548/524
[58] Field of Search ............... 548/251, 253, 548/254; 504/209

[56] References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,956,469 | 9/1990 | Covey et al. | 548/251 |
| 5,003,075 | 3/1991 | Covey et al. | 548/251 |
| 5,019,152 | 5/1991 | Covey et al. | 71/92 |
| 5,342,954 | 8/1994 | Goto et al. | 548/251 |
| 5,344,814 | 9/1994 | Goto et al. | 548/251 |
| 5,347,009 | 9/1994 | Goto et al. | 548/251 |
| 5,347,010 | 9/1994 | Goto et al. | 548/251 |
| 5,362,704 | 11/1994 | Goto et al. | 504/134 |

OTHER PUBLICATIONS

Aldrich Catalog, 1992.
JACS, 61, 3289–3291 (1939).

*Primary Examiner*—Johann Richter
*Assistant Examiner*—Jane C. Osswecki
*Attorney, Agent, or Firm*—Sprung Kramer Schaefer & Briscoe

[57] ABSTRACT

Novel herbicidal tetrazolinone derivatives of the formula

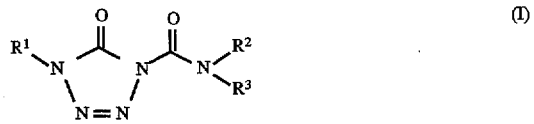

(I)

and intermediates therefor of the formula

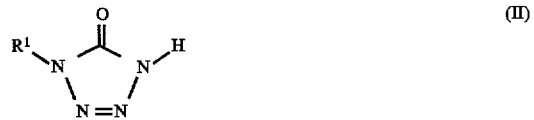

(II)

wherein $R^1$ is alkyl substituted by halogen, and $R^2$ and $R^3$ each independently is alkyl, alkenyl, alkynyl, cycloalkyl, phenyl or substituted phenyl, or $R^2$ and $R^3$ together with the N-atom to which they are attached, which may form a 5- or 6-membered heterocyclic ring.

11 Claims, No Drawings

TETRAZOLINONES

TETRAZOLINONES

The present invention relates to tetrazolinone derivatives substituted by haloalkyl group, to a process for their preparation, to their use as herbicides, as well as to novel intermediates for their preparation and to processes for their preparation.

It is known that a group of certain 1-alkyltetrazolinone derivatives have herbicidal activities [See: U.S. Pat. Nos. 4,618,365 (=EP 146279-A), 4,826,529, 4,830,661, 4,956,469, 5,003,075, 5,019,152, 5,120,346, 5,342,954, 5,344,814, 5,347,009, 5,347,010 and 5,362,704].

There have now been found novel tetrazolinone derivatives represented by the following formula:

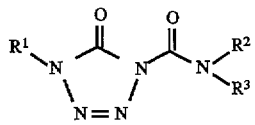

wherein, $R^1$ is alkyl substituted by halogen, and $R^2$ and $R^3$ each independently is alkyl, alkenyl, alkynyl, cycloalkyl which may optionally be substituted, phenyl or substituted phenyl, or $R^2$ and $R^3$ together with the N-atom to which they are attached, are a 5- or 6-membered heterocyclic ring which may be substituted.

The tetrazolinone derivatives of the formula (I) are obtained
when
(a) compounds of the formula

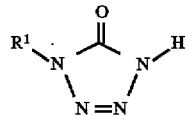

wherein $R^1$ has the same definition as above,
are reacted with compounds represented by the formula:

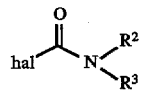

wherein $R^2$ and $R^3$ have the same definitions as above and hal is chlorine or bromine, in the presence of acid binders,
if appropriate in the presence of catalysts, and
if appropriate in the presence of inert solvents.

The tetrazolinone derivatives of formula (I) have strong herbicidal activities and are useful as herbicides.

Surprisingly the tetrazolinone derivatives of above formula (I) exhibit superior herbicidal activity to compounds known from the above-mentioned U.S. Pat. Nos. 4,618,365 (=European Pat. Application No. 146279-A), 4,826,529, 4,830,661, 4,956,469, 5,003,075, 5,019,152 and 5,120,346.

In this specification, the "alkyl substituted by halogen" comprises alkyl groups preferably having 1 to 6 carbon atoms in straight chain or branched chain substituted by 1 or more of fluorine, chlorine, bromine or iodine and, in the cases where a plural number of halogens exist, the halogen atoms may be either the same or different. Such halogen-substituted alkyl groups are exemplified by chloromethyl, bromomethyl, fluoromethyl, dichloromethyl, difluoromethyl, trichloromethyl, trifluoromethyl, chloro-difluoromethyl, 1-chloroethyl, 1-bromoethyl, 1-fluoro-ethyl, 2-chloroethyl, 2-bromoethyl, 2-fluoroethyl, 1,1-dichloroethyl, 1,2-dichloroethyl, 2,2-dichloroethyl, 1,1-difluoroethyl, 1,2-difluoroethyl, 2,2-difluoroethyl, 2,2-dibromoethyl, 2,2,2-trichloroethyl, 2,2,2-trifluoroethyl, perfluoroethyl, 1,1,2,2-tetrafluoroethyl, 2-chloro-1,1,2,2-tetrafluoroethyl, 2,3-dichloro-1,1,2,3,3-penta-fluoropropyl, 3-chloropropyl, 3-fluoropropyl, 3-bromo-propyl, 2,2,3,3,3-pentafluoropropyl, perfluoropropyl, and the like.

The "alkyl" comprises alkyl groups in straight chain or branched chain preferably having 1 to 8 carbon atoms and is exemplified by methyl, ethyl, propyl, isopropyl, n-, iso-, sec- or tert-butyl, n-, iso-, sec-, tert- or neo-pentyl, n-, iso-, sec-, tert- or neo-hexyl, heptyl, octyl, and the like.

The "alkenyl" comprises alkenyl groups in straight chain or branched chain preferably having 2 to 8 carbon atoms and is exemplified by vinyl, allyl, isopropenyl, 1-methyl-2-propenyl, 2- or 3-butenyl, 2-, 3- or 4-pentenyl, and the like.

The "alkynyl" comprises alkynyl groups in straight chain or branched chain preferably having 3 to 8 carbon atoms and is exemplified by propargyl, 1-methyl-2-propynyl, 2- or 3-butynyl, 2-, 3- or 4-pentynyl, and the like.

The "cycloalkyl" comprises alkyl groups in cyclic ring form having preferably 3 to 8 of carbon atoms and is exemplified by cyclopropyl, cyclobutyl, cyclopentyl, cyclohexyl, cycloheptyl, cyclooctyl, and the like, and such cycloalkyls may optionally be substituted. The substituent may be, for example, alkyl (such as methyl, ethyl, propyl, isopropyl, n-, iso-, sec- or tert-butyl or the like).

The substituted phenyl comprises phenyls having at least one substituent on the ring and, in cases where a plural number of substituents exist, such substituents may be either the same or different. The possible substituents comprise, for example, halogen (comprising fluorine, chlorine, bromine and iodine preferably fluorine, chlorine or bromine), cyano, nitro, alkyl (such as methyl, ethyl, propyl, isopropyl, n-, iso-, sec- or tert-butyl, and the like), haloalkyl (methyl, ethyl, propyl, isopropyl, n-, iso-, sec- or tert-butyl, and the like respectively substituted by at least one of fluorine, chlorine, bromine and iodine), alkoxy (such as methoxy, ethoxy, propoxy, isopropoxy, n-, iso-, sec- or tert-butoxy, and the like), haloalkoxy (such as methoxy, ethoxy, propoxy, isopropoxy, n-, iso-, sec- or tert-butoxy, and the like, respectively substituted by at least one of fluorine, chlorine, bromine and iodine), alkylthio (such as methylthio, ethylthio, propylthio, isopropylthio and n-, iso-, sec- or tert-butylthio), haloalkylthio (such as methylthio, ethylthio, propylthio, isopropylthio, n-, iso-, sec- or tert-butylthio, respectively substituted by at least one of fluorine, chlorine, bromine and iodine), and others.

The 5- or 6-membered heterocyclic ring comprises heterocyclic rings which contain at least one nitrogen atom as the heteroatom and may optionally contain a further heteroatom selected from the group consisting of nitrogen, oxygen and sulfur. Such heterocyclic rings may optionally be substituted by alkyl and further may be optionally condensed with a cyclic hydrocarbon group. Examples thereof include pyrrolidino, pyrrolyl, imidazolidinyl, piperidino, morpholino, pyrazolyl, indol-1-yl, perhydroindol-1-yl, 1,2,3,4-tetrahydroquinolin-1-yl, 2-methyl-1,1,2,2-tetra-hydroquinolin-1-yl, perhydroquinolin-1-yl, and the like.

Among the tetrazolinone derivatives according to the invention, of the formula (I), preferred compounds are those in which $R^1$ is $C_{1-6}$ alkyl which is substituted by one or more of fluorine, chlorine or bromine, and $R^2$ and $R^3$ each independently is $C_{1-6}$ alkyl, $C_{2-6}$ alkenyl, $C_{3-6}$ alkynyl, $C_{3-8}$ cycloalkyl which may optionally be substituted by $C_{1-6}$ alkyl, phenyl, or phenyl having at least one substituent selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ alkylthio and $C_{1-4}$ haloalkylthio, or $R^2$ and $R^3$ together with the N-atom to which they are attached, are a 5- or 6-membered saturated heterocyclic ring, optionally substituted by alkyl and/or condensed with a cyclic hydrocarbon.

Very particularly preferred tetrazolinone derivatives of the formula (I) are those
in which $R^1$ is $C_{1-3}$ alkyl which is substituted by one or more of fluorine, chlorine or bromine, and $R^2$ and $R^3$ each independently is $C_{1-4}$ alkyl, cyclopropyl which may optionally be substituted by methyl, cyclopentyl which may optionally be substituted by methyl, cyclohexyl which may optionally be substituted by methyl, allyl, propargyl, phenyl, or phenyl having at least one substituent selected from the group consisting of fluorine, chlorine, bromine, methyl, ethyl, methoxy, methylthio, nitro, cyano, trifluoromethyl, trifluoromethoxy, difluoromethoxy, 2,2,2-trifluoroethoxy, trifluoromethylthio and 2,2,2-trifluoro-ethylthio, or $R^2$ and $R^3$ together with the N-atom to which they are attached, are piperidino, methylpiperidino, morpholino, indol-1-yl, perhydroindol-1-yl, 1,2,3,4-tetrahydro-quinolin-1-yl, 2-methyl-1,2,3,4-tetrahydroquinolin-1-yl or perhydroquinolin-1-yl.

Specific tetrazolinone derivatives of formula (I) are shown in the following Table 1 and Table 2. Table 1 illustrates tetrazolinone derivatives of formula (I) in which $R^1$ and $R^2$ are groups which are independent of each other and Table 2 illustrates tetrazolinone derivatives of formula (I) in which $R^1$ and $R^2$ are a heterocyclic ring together with the N-atom to which they are attached.

TABLE 1

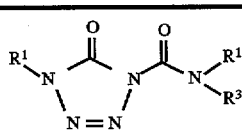

| $R^1$ | $R^2$ | $R^3$ |
|---|---|---|
| ClCH$_2$ | ethyl | ethyl |
| ClCH$_2$ | ethyl | cyclohexyl |
| ClCH$_2$ | n-propyl | n-propyl |
| ClCH$_2$ | n-propyl | cyclopropyl |
| ClCH$_2$ | n-propyl | cyclopentyl |
| ClCH$_2$ | allyl | allyl |
| ClCH$_2$ | propargyl | propargyl |
| ClCH$_2$ | isopropyl | phenyl |
| ClCH$_2$ | isopropyl | 2-fluorophenyl |
| ClCH$_2$ | isopropyl | 3-fluorophenyl |
| ClCH$_2$ | isopropyl | 4-fluorophenyl |
| ClCH$_2$ | isopropyl | 2-chlorophenyl |
| ClCH$_2$ | isopropyl | 3-chlorophenyl |
| ClCH$_2$ | isopropyl | 4-chlorophenyl |
| ClCH$_2$ | isopropyl | 2,3-dichlorophenyl |
| ClCH$_2$ | isopropyl | 2,4-dichlorophenyl |
| ClCH$_2$ | isopropyl | 2,5-dichlorophenyl |
| ClCH$_2$ | isopropyl | 2,6-dichlorophenyl |
| ClCH$_2$ | isopropyl | 3,4-dichlorophenyl |
| ClCH$_2$ | isopropyl | 3,5-dichlorophenyl |
| ClCH$_2$ | isopropyl | 2,4,6-trichlorophenyl |
| ClCH$_2$ | isopropyl | 2-chloro-3-methylphenyl |

TABLE 1-continued

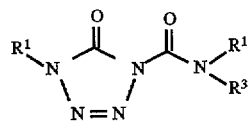

| $R^1$ | $R^2$ | $R^3$ |
|---|---|---|
| ClCH$_2$ | isopropyl | 2-chloro-4-methylphenyl |
| ClCH$_2$ | isopropyl | 2-chloro-5-methylphenyl |
| ClCH$_2$ | isopropyl | 2-chloro-6-methylphenyl |
| ClCH$_2$ | isopropyl | 3-chloro-4-methylphenyl |
| ClCH$_2$ | isopropyl | 3-chloro-4-trifluoromethylphenyl |
| ClCH$_2$ | isopropyl | 3-chloro-4-trifluromethoxyphenyl |
| ClCH$_2$ | isopropyl | 3-chloro-4-trifluoromethylthiophenyl |
| ClCH$_2$ | isopropyl | 2-bromophenyl |
| ClCH$_2$ | isopropyl | 2-trifluoromethylphenyl |
| ClCH$_2$ | isopropyl | 3-trifluoromethylphenyl |
| ClCH$_2$ | isopropyl | 4-trifluoromethylphenyl |
| ClCH$_2$ | isopropyl | 2-trifluromethoxyphenyl |
| ClCH$_2$ | isopropyl | 2-difluoromethoxyphenyl |
| ClCH$_2$ | isopropyl | 2-(2,2,2-trifluoroethoxy)phenyl |
| ClCH$_2$ | isopropyl | 2 trifluoromethylthiophenyl |
| ClCH$_2$ | isopropyl | 2-(2,2,2-trifluoroethylthio)phenyl |
| ClCH$_2$ | isopropyl | 2-methylphenyl |
| ClCH$_2$ | isopropyl | 3-methylphenyl |
| ClCH$_2$ | isopropyl | 4-methylphenyl |
| ClCH$_2$ | isopropyl | 2,3-dimethylphenyl |
| ClCH$_2$ | isopropyl | 2,4-dimethylphenyl |
| ClCH$_2$ | isopropyl | 2,5-dimethylphenyl |
| ClCH$_2$ | isopropyl | 2,6-dimethylphenyl |
| ClCH$_2$ | isopropyl | 2,4,6-trimethylphenyl |
| ClCH$_2$ | isopropyl | 2-ethylphenyl |
| ClCH$_2$ | isopropyl | 3-ethylphenyl |
| ClCH$_2$ | isopropyl | 4-ethylphenyl |
| ClCH$_2$ | isopropyl | 2-methoxyphenyl |
| ClCH$_2$ | isopropyl | 3-methoxyphenyl |
| ClCH$_2$ | isopropyl | 4-methoxyphenyl |
| ClCH$_2$ | isopropyl | 2-methylthiophenyl |
| ClCH$_2$ | isopropyl | 2-nitrophenyl |
| ClCH$_2$ | isopropyl | 2-cyanophenyl |
| BrCH$_2$ | ethyl | ethyl |
| BrCH$_2$ | ethyl | cyclohexyl |
| BrCH$_2$ | n-propyl | n-propyl |
| BrCH$_2$ | n-propyl | cyclopropyl |
| BrCH$_2$ | n-propyl | cyclopentyl |
| BrCH$_2$ | allyl | allyl |
| BrCH$_2$ | propargyl | propargyl |
| BrCH$_2$ | methyl | phenyl |
| BrCH$_2$ | ethyl | phenyl |
| BrCH$_2$ | n-propyl | phenyl |
| BrCH$_2$ | isopropyl | phenyl |
| BrCH$_2$ | n-butyl | phenyl |
| BrCH$_2$ | s-butyl | phenyl |
| BrCH$_2$ | isobutyl | phenyl |
| BrCH$_2$ | phenyl | phenyl |
| BrCH$_2$ | isopropyl | 2-fluorophenyl |
| BrCH$_2$ | isopropyl | 3-fluorophenyl |
| BrCH$_2$ | isopropyl | 4-fluorophenyl |
| BrCH$_2$ | isopropyl | 2-chlorophenyl |
| BrCH$_2$ | isopropyl | 3-chlorophenyl |
| BrCH$_2$ | isopropyl | 4-chlorophenyl |
| BrCH$_2$ | isopropyl | 2,3-dichlorophenyl |
| BrCH$_2$ | isopropyl | 2,4-dichlorophenyl |
| BrCH$_2$ | isopropyl | 2,5-dichlorophenyl |
| BrCH$_2$ | isopropyl | 2,6-dichlorophenyl |
| BrCH$_2$ | isopropyl | 3,4-dichlorophenyl |
| BrCH$_2$ | isopropyl | 3,5-dichlorophenyl |
| BrCH$_2$ | isopropyl | 2,4,6-trichlorophenyl |
| BrCH$_2$ | isopropyl | 2-chloro-3-methylphenyl |
| BrCH$_2$ | isopropyl | 2-chloro-4-methylphenyl |
| BrCH$_2$ | isopropyl | 2-chloro-5-methylphenyl |
| BrCH$_2$ | isopropyl | 2-chloro-6-methylphenyl |
| BrCH$_2$ | isopropyl | 3-chloro-4-methylphenyl |
| BrCH$_2$ | isopropyl | 3-chloro-4-trifluoromethylphenyl |
| BrCH$_2$ | isopropyl | 3-chloro-4-trifluromethoxyphenyl |
| BrCH$_2$ | isopropyl | 3-chloro-4-trifluoromethylthiophenyl |
| BrCH$_2$ | isopropyl | 2-bromophenyl |

TABLE 1-continued

| R¹ | R² | R³ |
|---|---|---|
| BrCH₂ | isopropyl | 2-trifluoromethylphenyl |
| BrCH₂ | isopropyl | 3-trifluoromethylphenyl |
| BrCH₂ | isopropyl | 4-trifluoromethylphenyl |
| BrCH₂ | isopropyl | 2-trifluromethoxyphenyl |
| BrCH₂ | isopropyl | 2-difluoromethoxyphenyl |
| BrCH₂ | isopropyl | 2-(2,2,2-trifluoroethoxy)phenyl |
| BrCH₂ | isopropyl | 2-trifluoromethylthiophenyl |
| BrCH₂ | isopropyl | 2-(2,2,2-trifluoroethylthio)phenyl |
| BrCH₂ | isopropyl | 2-methylphenyl |
| BrCH₂ | isopropyl | 3-methylphenyl |
| BrCH₂ | isopropyl | 4-methylphenyl |
| BrCH₂ | isopropyl | 2,3-dimethylphenyl |
| BrCH₂ | isopropyl | 2,4-dimethylphenyl |
| BrCH₂ | isopropyl | 2,5-dimethylphenyl |
| BrCH₂ | isopropyl | 2,6-dimethylphenyl |
| BrCH₂ | isopropyl | 2,4,6-trimethylphenyl |
| BrCH₂ | isopropyl | 2-ethylphenyl |
| BrCH₂ | isopropyl | 3-ethylphenyl |
| BrCH₂ | isopropyl | 4-ethylphenyl |
| BrCH₂ | isopropyl | 2-methoxyphenyl |
| BrCH₂ | isopropyl | 3-methoxyphenyl |
| BrCH₂ | isopropyl | 4-methoxyphenyl |
| BrCH₂ | isopropyl | 2-methylthiophenyl |
| BrCH₂ | isopropyl | 2-nitrophenyl |
| BrCH₂ | isopropyl | 2-cyanophenyl |
| FCH₂ | ethyl | ethyl |
| FCH₂ | ethyl | cyclohexyl |
| FCH₂ | n-propyl | n-propyl |
| FCH₂ | n-propyl | cyclopropyl |
| FCH₂ | n-propyl | cyclopentyl |
| FCH₂ | allyl | allyl |
| FCH₂ | propargyl | propargyl |
| FCH₂ | methyl | phenyl |
| FCH₂ | ethyl | phenyl |
| FCH₂ | n-propyl | phenyl |
| FCH₂ | isopropyl | phenyl |
| FCH₂ | n-butyl | phenyl |
| FCH₂ | s-butyl | phenyl |
| FCH₂ | isobutyl | phenyl |
| FCH₂ | phenyl | phenyl |
| FCH₂ | isopropyl | 2-fluorophenyl |
| FCH₂ | isopropyl | 3-fluorophenyl |
| FCH₂ | isopropyl | 4-fluorophenyl |
| FCH₂ | isopropyl | 2-chlorophenyl |
| FCH₂ | isopropyl | 3-chlorophenyl |
| FCH₂ | isopropyl | 4-chlorophenyl |
| FCH₂ | isopropyl | 2,3-dichlorophenyl |
| FCH₂ | isopropyl | 2,4-dichlorophenyl |
| FCH₂ | isopropyl | 2,5-dichlorophenyl |
| FCH₂ | isopropyl | 2,6-dichlorophenyl |
| FCH₂ | isopropyl | 3,4-dichlorophenyl |
| FCH₂ | isopropyl | 3,5-dichlorophenyl |
| FCH₂ | isopropyl | 2,4,6-trichlorophenyl |
| FCH₂ | isopropyl | 2-chloro-3-methylphenyl |
| FCH₂ | isopropyl | 2-chloro-4-methylphenyl |
| FCH₂ | isopropyl | 2-chloro-5-methylphenyl |
| FCH₂ | isopropyl | 2-chloro-6-methylphenyl |
| FCH₂ | isopropyl | 3-chloro-4-methylphenyl |
| FCH₂ | isopropyl | 3-chloro-4-trifluoromethylphenyl |
| FCH₂ | isopropyl | 3-chloro-4-trifluromethoxyphenyl |
| FCH₂ | isopropyl | 3-chloro-4-trifluoromethylthiophenyl |
| FCH₂ | isopropyl | 2-bromophenyl |
| FCH₂ | isopropyl | 2-trifluoromethylphenyl |
| FCH₂ | isopropyl | 3-trifluoromethylphenyl |
| FCH₂ | isopropyl | 4-trifluoromethylphenyl |
| FCH₂ | isopropyl | 2-trifluromethoxyphenyl |
| FCH₂ | isopropyl | 2-difluoromethoxyphenyl |
| FCH₂ | isopropyl | 2-(2,2,2-trifluoroethoxy)phenyl |
| FCH₂ | isopropyl | 2-trifluoromethylthiophenyl |
| FCH₂ | isopropyl | 2-(2,2,2-trifluoroethylthio)phenyl |
| FCH₂ | isopropyl | 2-methylphenyl |
| FCH₂ | isopropyl | 3-methylphenyl |
| FCH₂ | isopropyl | 4-methylphenyl |
| FCH₂ | isopropyl | 2,3-dimethylphenyl |
| FCH₂ | isopropyl | 2,4-dimethylphenyl |
| FCH₂ | isopropyl | 2,5-dimethylphenyl |
| FCH₂ | isopropyl | 2,6-dimethylphenyl |
| FCH₂ | isopropyl | 2,4,6-trimethylphenyl |
| FCH₂ | isopropyl | 2-ethylphenyl |
| FCH₂ | isopropyl | 3-ethylphenyl |
| FCH₂ | isopropyl | 4-ethylphenyl |
| FCH₂ | isopropyl | 2-methoxyphenyl |
| FCH₂ | isopropyl | 3-methoxyphenyl |
| FCH₂ | isopropyl | 4-methoxyphenyl |
| FCH₂ | isopropyl | 2-methylthiophenyl |
| FCH₂ | isopropyl | 2-nitrophenyl |
| FCH₂ | isopropyl | 2-cyanophenyl |
| Cl₂HC | ethyl | ethyl |
| Cl₂HC | ethyl | cyclohexyl |
| Cl₂HC | ethyl | 2-methylcyclohexyl |
| Cl₂HC | n-propyl | n-propyl |
| Cl₂HC | n-propyl | cyclopropyl |
| Cl₂HC | n-propyl | cyclopentyl |
| Cl₂HC | allyl | allyl |
| Cl₂HC | propargyl | propargyl |
| Cl₂HC | methyl | phenyl |
| Cl₂HC | ethyl | phenyl |
| Cl₂HC | n-propyl | phenyl |
| Cl₂HC | isopropyl | phenyl |
| Cl₂HC | n-butyl | phenyl |
| Cl₂HC | s-butyl | phenyl |
| Cl₂HC | isobutyl | phenyl |
| Cl₂HC | phenyl | phenyl |
| Cl₂HC | isopropyl | 2-fluorophenyl |
| Cl₂HC | isopropyl | 3-fluorophenyl |
| Cl₂HC | isopropyl | 4-fluorophenyl |
| Cl₂HC | isopropyl | 2-chlorophenyl |
| Cl₂HC | isopropyl | 3-chlorophenyl |
| Cl₂HC | isopropyl | 4-chlorophenyl |
| Cl₂HC | isopropyl | 2,3-dichlorophenyl |
| Cl₂HC | isopropyl | 2,4-dichlorophenyl |
| Cl₂HC | isopropyl | 2,5-dichlorophenyl |
| Cl₂HC | isopropyl | 2,6-dichlorophenyl |
| Cl₂HC | isopropyl | 3,4-dichlorophenyl |
| Cl₂HC | isopropyl | 3,5-dichlorophenyl |
| Cl₂HC | isopropyl | 2,4,6-trichlorophenyl |
| Cl₂HC | isopropyl | 2-chloro-3-methylphenyl |
| Cl₂HC | isopropyl | 2-chloro-4-methylphenyl |
| Cl₂HC | isopropyl | 2-chloro-5-methylphenyl |
| Cl₂HC | isopropyl | 2-chloro-6-methylphenyl |
| Cl₂HC | isopropyl | 3-chloro-4-methylphenyl |
| Cl₂HC | isopropyl | 3-chloro-4-trifluoromethylphenyl |
| Cl₂HC | isopropyl | 3-chloro-4-trifluromethoxyphenyl |
| Cl₂HC | isopropyl | 3-chloro-4-trifluoromethylthiophenyl |
| Cl₂HC | isopropyl | 2-bromophenyl |
| Cl₂HC | isopropyl | 2-trifluoromethylphenyl |
| Cl₂HC | isopropyl | 3-trifluoromethylphenyl |
| Cl₂HC | isopropyl | 4-trifluoromethylphenyl |
| Cl₂HC | isopropyl | 2-trifluromethoxyphenyl |
| Cl₂HC | isopropyl | 2-difluoromethoxyphenyl |
| Cl₂HC | isopropyl | 2-(2,2,2-trifluoroethoxy)phenyl |
| Cl₂HC | isopropyl | 2-(2,2,2-trifluoroethylthio)phenyl |
| Cl₂HC | isopropyl | 2-trifluoromethylthiophenyl |
| Cl₂HC | isopropyl | 2-methylphenyl |
| Cl₂HC | isopropyl | 3-methylphenyl |
| Cl₂HC | isopropyl | 4-methylphenyl |
| Cl₂HC | isopropyl | 2,3-dimethylphenyl |
| Cl₂HC | isopropyl | 2,4-dimethylphenyl |
| Cl₂HC | isopropyl | 2,5-dimethylphenyl |
| Cl₂HC | isopropyl | 2,6-dimethylphenyl |

TABLE 1-continued

| R¹ | R² | R³ |
|---|---|---|
| Cl₂HC | isopropyl | 2,4,6-trimethylphenyl |
| Cl₂HC | isopropyl | 2-ethylphenyl |
| Cl₂HC | isopropyl | 3-ethylphenyl |
| Cl₂HC | isopropyl | 4-ethylphenyl |
| Cl₂HC | isopropyl | 2-methoxyphenyl |
| Cl₂HC | isopropyl | 3-methoxyphenyl |
| Cl₂HC | isopropyl | 4-methoxyphenyl |
| Cl₂HC | isopropyl | 2-methylthiophenyl |
| Cl₂HC | isopropyl | 2-nitrophenyl |
| Cl₂HC | isopropyl | 2-cyanophenyl |
| F₂HC | ethyl | ethyl |
| F₂HC | ethyl | cyclohexyl |
| F₂HC | n-propyl | n-propyl |
| F₂HC | n-propyl | cyclopropyl |
| F₂HC | n-propyl | cyclopentyl |
| F₂HC | allyl | allyl |
| F₂HC | propargyl | propargyl |
| F₂HC | methyl | phenyl |
| F₂HC | ethyl | phenyl |
| F₂HC | n-propyl | phenyl |
| F₂HC | isopropyl | phenyl |
| F₂HC | n-butyl | phenyl |
| F₂HC | s-butyl | phenyl |
| F₂HC | isobutyl | phenyl |
| F₂HC | phenyl | phenyl |
| F₂HC | isopropyl | 2-fluorophenyl |
| F₂HC | isopropyl | 3-fluorophenyl |
| F₂HC | isopropyl | 4-fluorophenyl |
| F₂HC | isopropyl | 2-chlorophenyl |
| F₂HC | isopropyl | 3-chlorophenyl |
| F₂HC | isopropyl | 4-chlorophenyl |
| F₂HC | isopropyl | 2,3-dichlorophenyl |
| F₂HC | isopropyl | 2,4-dichlorophenyl |
| F₂HC | isopropyl | 2,5-dichlorophenyl |
| F₂HC | isopropyl | 2,6-dichlorophenyl |
| F₂HC | isopropyl | 3,4-dichlorophenyl |
| F₂HC | isopropyl | 3,5-dichlorophenyl |
| F₂HC | isopropyl | 2,4,6-trichlorophenyl |
| F₂HC | isopropyl | 2-chloro-3-methylphenyl |
| F₂HC | isopropyl | 2-chloro-4-methylphenyl |
| F₂HC | isopropyl | 2-chloro-5-methylphenyl |
| F₂HC | isopropyl | 2-chloro-6-methylphenyl |
| F₂HC | isopropyl | 3-chloro-4-methylphenyl |
| F₂HC | isopropyl | 3-chloro-4-trifluoromethylphenyl |
| F₂HC | isopropyl | 3-chloro-4-trifluromethoxyphenyl |
| F₂HC | isopropyl | 3-chloro-4-trifluoromethylthiophenyl |
| F₂HC | isopropyl | 2-bromophenyl |
| F₂HC | isopropyl | 2-trifluoromethylphenyl |
| F₂HC | isopropyl | 3-trifluoromethylphenyl |
| F₂HC | isopropyl | 4-trifluoromethylphenyl |
| F₂HC | isopropyl | 2-trifluromethoxyphenyl |
| F₂HC | isopropyl | 2-difluoromethoxyphenyl |
| F₂HC | isopropyl | 2-(2,2,2-trifluoroethoxy)phenyl |
| F₂HC | isopropyl | 2-(2,2,2-trifluoroethylthio)phenyl |
| F₂HC | isopropyl | 2-trifluoromethylthiophenyl |
| F₂HC | isopropyl | 2-methylphenyl |
| F₂HC | isopropyl | 3-methylphenyl |
| F₂HC | isopropyl | 4-methylphenyl |
| F₂HC | isopropyl | 2,3-dimethylphenyl |
| F₂HC | isopropyl | 2,4-dimethylphenyl |
| F₂HC | isopropyl | 2,5-dimethylphenyl |
| F₂HC | isopropyl | 2,6-dimethylphenyl |
| F₂HC | isopropyl | 2,4,6-trimethylphenyl |
| F₂HC | isopropyl | 2-ethylphenyl |
| F₂HC | isopropyl | 3-ethylphenyl |
| F₂HC | isopropyl | 4-ethylphenyl |
| F₂HC | isopropyl | 2-methoxyphenyl |
| F₂HC | isopropyl | 3-methoxyphenyl |
| F₂HC | isopropyl | 4-methoxyphenyl |
| F₂HC | isopropyl | 2-methylthiophenyl |
| F₂HC | isopropyl | 2-nitrophenyl |
| F₂HC | isopropyl | 2-cyanophenyl |
| Cl₃C | ethyl | ethyl |
| Cl₃C | ethyl | cyclohexyl |
| Cl₃C | n-propyl | n-propyl |
| Cl₃C | n-propyl | cyclopropyl |
| Cl₃C | n-propyl | cyclopentyl |
| Cl₃C | allyl | allyl |
| Cl₃C | propargyl | propargyl |
| Cl₃C | methyl | phenyl |
| Cl₃C | ethyl | phenyl |
| Cl₃C | n-propyl | phenyl |
| Cl₃C | isopropyl | phenyl |
| Cl₃C | n-butyl | phenyl |
| Cl₃C | s-butyl | phenyl |
| Cl₃C | isobutyl | phenyl |
| Cl₃C | phenyl | phenyl |
| Cl₃C | isopropyl | 2-fluorophenyl |
| Cl₃C | isopropyl | 3-fluorophenyl |
| Cl₃C | isopropyl | 4-fluorophenyl |
| Cl₃C | isopropyl | 2-chlorophenyl |
| Cl₃C | isopropyl | 3-chlorophenyl |
| Cl₃C | isopropyl | 4-chlorophenyl |
| Cl₃C | isopropyl | 2,3-dichlorophenyl |
| Cl₃C | isopropyl | 2,4-dichlorophenyl |
| Cl₃C | isopropyl | 2,5-dichlorophenyl |
| Cl₃C | isopropyl | 2,6-dichlorophenyl |
| Cl₃C | isopropyl | 3,4-dichlorophenyl |
| Cl₃C | isopropyl | 3,5-dichlorophenyl |
| Cl₃C | isopropyl | 2,4,6-trichlorophenyl |
| Cl₃C | isopropyl | 2-chloro-3-methylphenyl |
| Cl₃C | isopropyl | 2-chloro-4-methylphenyl |
| Cl₃C | isopropyl | 2-chloro-5-methylphenyl |
| Cl₃C | isopropyl | 2-chloro-6-methylphenyl |
| Cl₃C | isopropyl | 3-chloro-4-methylphenyl |
| Cl₃C | isopropyl | 3-chloro-4-trifluoromethylphenyl |
| Cl₃C | isopropyl | 3-chloro-4-trifluromethoxyphenyl |
| Cl₃C | isopropyl | 3-chloro-4-trifluoromethylthiophenyl |
| Cl₃C | isopropyl | 2-bromophenyl |
| Cl₃C | isopropyl | 2-trifluoromethylphenyl |
| Cl₃C | isopropyl | 3-trifluoromethylphenyl |
| Cl₃C | isopropyl | 4-trifluoromethylphenyl |
| Cl₃C | isopropyl | 2-trifluromethoxyphenyl |
| Cl₃C | isopropyl | 2-(2,2,2-trifluoroethoxy)phenyl |
| Cl₃C | isopropyl | 2-difluoromethoxyphenyl |
| Cl₃C | isopropyl | 2-(2,2,2-trifluoroethylthio)phenyl |
| Cl₃C | isopropyl | 2-trifluoromethylthiophenyl |
| Cl₃C | isopropyl | 2-methylphenyl |
| Cl₃C | isopropyl | 3-methylphenyl |
| Cl₃C | isopropyl | 4-methylphenyl |
| Cl₃C | isopropyl | 2,3-dimethylphenyl |
| Cl₃C | isopropyl | 2,4-dimethylphenyl |
| Cl₃C | isopropyl | 2,5-dimethylphenyl |
| Cl₃C | isopropyl | 2,6-dimethylphenyl |
| Cl₃C | isopropyl | 2,4,6-trimethylphenyl |
| Cl₃C | isopropyl | 2-ethylphenyl |
| Cl₃C | isopropyl | 3-ethylphenyl |
| Cl₃C | isopropyl | 4-ethylphenyl |
| Cl₃C | isopropyl | 2-methoxyphenyl |
| Cl₃C | isopropyl | 3-methoxyphenyl |
| Cl₃C | isopropyl | 4-methoxyphenyl |
| Cl₃C | isopropyl | 2-methylthiophenyl |
| Cl₃C | isopropyl | 2-nitrophenyl |
| Cl₃C | isopropyl | 2-cyanophenyl |
| F₃C | ethyl | ethyl |
| F₃C | ethyl | cyclohexyl |
| F₃C | n-propyl | n-propyl |
| F₃C | n-propyl | cyclopropyl |
| F₃C | n-propyl | cyclopentyl |
| F₃C | allyl | allyl |

TABLE 1-continued

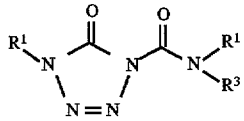

| R¹ | R² | R³ |
|---|---|---|
| F₃C | propargyl | propargyl |
| F₃C | methyl | phenyl |
| F₃C | ethyl | phenyl |
| F₃C | n-propyl | phenyl |
| F₃C | isopropyl | phenyl |
| F₃C | n-butyl | phenyl |
| F₃C | s-butyl | phenyl |
| F₃C | isobutyl | phenyl |
| F₃C | phenyl | phenyl |
| F₃C | isopropyl | 2-fluorophenyl |
| F₃C | isopropyl | 3-fluorophenyl |
| F₃C | isopropyl | 4-fluorophenyl |
| F₃C | isopropyl | 2-chlorophenyl |
| F₃C | isopropyl | 3-chlorophenyl |
| F₃C | isopropyl | 4-chlorophenyl |
| F₃C | isopropyl | 2,3-dichlorophenyl |
| F₃C | isopropyl | 2,4-dichlorophenyl |
| F₃C | isopropyl | 2,5-dichlorophenyl |
| F₃C | isopropyl | 2,6-dichlorophenyl |
| F₃C | isopropyl | 3,4-dichlorophenyl |
| F₃C | isopropyl | 3,5-dichlorophenyl |
| F₃C | isopropyl | 2,4,6-trichlorophenyl |
| F₃C | isopropyl | 2-chloro-3-methylphenyl |
| F₃C | isopropyl | 2-chloro-4-methylphenyl |
| F₃C | isopropyl | 2-chloro-5-methylphenyl |
| F₃C | isopropyl | 2-chloro-6-methylphenyl |
| F₃C | isopropyl | 3-chloro-4-methylphenyl |
| F₃C | isopropyl | 3-chloro-4-trifluoromethylphenyl |
| F₃C | isopropyl | 3-chloro-4-trifluromethoxyphenyl |
| F₃C | isopropyl | 3-chloro-4-trifluoromethylthiophenyl |
| F₃C | isopropyl | 2-bromophenyl |
| F₃C | isopropyl | 2-trifluoromethylphenyl |
| F₃C | isopropyl | 3-trifluoromethylphenyl |
| F₃C | isopropyl | 4-trifluoromethylphenyl |
| F₃C | isopropyl | 2-trifluromethoxyphenyl |
| F₃C | isopropyl | 2-difluoromethoxyphenyl |
| F₃C | isopropyl | 2-(2,2,2-trifluoroethoxy)phenyl |
| F₃C | isopropyl | 2-(2,2,2-trifluoroethylthio)phenyl |
| F₃C | isopropyl | 2-trifluoromethylthiophenyl |
| F₃C | isopropyl | 2-methylphenyl |
| F₃C | isbpropyl | 3-methylphenyl |
| F₃C | isopropyl | 4-methylphenyl |
| F₃C | isopropyl | 2,3-dimethylphenyl |
| F₃C | isopropyl | 2,4-dimethylphenyl |
| F₃C | isopropyl | 2,5-dimethylphenyl |
| F₃C | isopropyl | 2,6-dimethylphenyl |
| F₃C | isopropyl | 2,4,6-trimethylphenyl |
| F₃C | isopropyl | 2-ethylphenyl |
| F₃C | isopropyl | 3-ethylphenyl |
| F₃C | isopropyl | 4-ethylphenyl |
| F₃C | isopropyl | 2-methoxyphenyl |
| F₃C | isopropyl | 3-methoxyphenyl |
| F₃C | isopropyl | 4-methoxyphenyl |
| F₃C | isopropyl | 2-methylthiophenyl |
| F₃C | isopropyl | 2-nitrophenyl |
| F₃C | isopropyl | 2-cyanophenyl |
| F₂ClC | ethyl | ethyl |
| F₂ClC | ethyl | cyclohexyl |
| F₂ClC | n-propyl | n-propyl |
| F₂ClC | n-propyl | cyclopropyl |
| F₂ClC | n-propyl | cyclopentyl |
| F₂ClC | allyl | allyl |
| F₂ClC | propargyl | propargyl |
| F₂ClC | methyl | phenyl |
| F₂ClC | ethyl | phenyl |
| F₂ClC | n-propyl | phenyl |
| F₂ClC | isopropyl | phenyl |
| F₂ClC | n-butyl | phenyl |
| F₂ClC | s-butyl | phenyl |
| F₂ClC | isobutyl | phenyl |

TABLE 1-continued

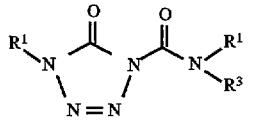

| R¹ | R² | R³ |
|---|---|---|
| F₂ClC | phenyl | phenyl |
| F₂ClC | isopropyl | 2-fluorophenyl |
| F₂ClC | isopropyl | 3-fluorophenyl |
| F₂ClC | isopropyl | 4-fluorophenyl |
| F₂ClC | isopropyl | 2-chlorophenyl |
| F₂ClC | isopropyl | 3-chlorophenyl |
| F₂ClC | isopropyl | 4-chlorophenyl |
| F₂ClC | isopropyl | 2,3-dichlorophenyl |
| F₂ClC | isopropyl | 2,4-dichlorophenyl |
| F₂ClC | isopropyl | 2,5-dichlorophenyl |
| F₂ClC | isopropyl | 2,6-dichlorophenyl |
| F₂ClC | isopropyl | 3,4-dichlorophenyl |
| F₂ClC | isopropyl | 3-5-dichlorophenyl |
| F₂ClC | isopropyl | 2,4,6-trichlorophenyl |
| F₂ClC | isopropyl | 2-chloro-3-methylphenyl |
| F₂ClC | isopropyl | 2-chloro-4-methylphenyl |
| F₂ClC | isopropyl | 2-chloro-5-methylphenyl |
| F₂ClC | isopropyl | 2-chloro-6-methylphenyl |
| F₂ClC | isopropyl | 3-chloro-4-methylphenyl |
| F₂ClC | isopropyl | 3-chloro-4-trifluoromethylphenyl |
| F₂ClC | isopropyl | 3-chloro-4-trifluromethoxyphenyl |
| F₂ClC | isopropyl | 3-chloro-4-trifluoromethylthiophenyl |
| F₂ClC | isopropyl | 2-bromophenyl |
| F₂ClC | isopropyl | 2-trifluoromethylphenyl |
| F₂ClC | isopropyl | 3-trifluoromethylphenyl |
| F₂ClC | isopropyl | 4-trifluoromethylphenyl |
| F₂ClC | isopropyl | 2-trifluromethoxyphenyl |
| F₂ClC | isopropyl | 2-difluoromethoxyphenyl |
| F₂ClC | isopropyl | 2-(2,2,2-trifluoroethoxy)phenyl |
| F₂ClC | isopropyl | 2-(2,2,2-trifluoroethylthio)phenyl |
| F₂ClC | isopropyl | 2-trifluoromethylthiophenyl |
| F₂ClC | isopropyl | 2-methylphenyl |
| F₂ClC | isopropyl | 3-methylphenyl |
| F₂ClC | isopropyl | 4-methylphenyl |
| F₂ClC | isopropyl | 2,3-dimethylphenyl |
| F₂ClC | isopropyl | 2,4-dimethylphenyl |
| F₂ClC | isopropyl | 2,5-dimethylphenyl |
| F₂ClC | isopropyl | 2,6-dimethylphenyl |
| F₂ClC | isopropyl | 2,4,6-trimethylphenyl |
| F₂ClC | isopropyl | 2-ethylphenyl |
| F₂ClC | isopropyl | 3-ethylphenyl |
| F₂ClC | isopropyl | 4-ethylphenyl |
| F₂ClC | isopropyl | 2-methoxyphenyl |
| F₂ClC | isopropyl | 3-methoxyphenyl |
| F₂ClC | isopropyl | 4-methoxyphenyl |
| F₂ClC | isopropyl | 2-methylthiophenyl |
| F₂ClC | isopropyl | 2-nitrophenyl |
| F₂ClC | isopropyl | 2-cyanophenyl |
| CH₃CHCl | ethyl | ethyl |
| CH₃CHCl | ethyl | cyclohexyl |
| CH₃CHCl | n-propyl | n-propyl |
| CH₃CHCl | n-propyl | cyclopropyl |
| CH₃CHCl | n-propyl | cyclopentyl |
| CH₃CHCl | allyl | allyl |
| CH₃CHCl | propargyl | propargyl |
| CH₃CHCl | methyl | phenyl |
| CH₃CHCl | ethyl | phenyl |
| CH₃CHCl | n-propyl | phenyl |
| CH₃CHCl | isopropyl | phenyl |
| CH₃CHCl | n-butyl | phenyl |
| CH₃CHCl | s-butyl | phenyl |
| CH₃CHCl | isobutyl | phenyl |
| CH₃CHCl | phenyl | phenyl |
| CH₃CHCl | isopropyl | 2-fluorophenyl |
| CH₃CHCl | isopropyl | 3-fluorophenyl |
| CH₃CHCl | isopropyl | 4-fluorophenyl |
| CH₃CHCl | isopropyl | 2-chlorophenyl |
| CH₃CHCl | isopropyl | 3-chlorophenyl |
| CH₃CHCl | isopropyl | 4-chlorophenyl |
| CH₃CHCl | isopropyl | 2,3-dichlorophenyl |

TABLE 1-continued

R¹–N(C(=O))–N(N=N)–C(=O)–N(R¹)(R³), with R² on the ring

| R¹ | R² | R³ |
|---|---|---|
| CH₃CHCl | isopropyl | 2,4-dichlorophenyl |
| CH₃CHCl | isopropyl | 2,5-dichlorophenyl |
| CH₃CHCl | isopropyl | 2,6-dichlorophenyl |
| CH₃CHCl | isopropyl | 3,4-dichlorophenyl |
| CH₃CHCl | isopropyl | 3,5-dichlorophenyl |
| CH₃CHCl | isopropyl | 2,4,6-trichlorophenyl |
| CH₃CHCl | isopropyl | 2-chloro-3-methylphenyl |
| CH₃CHCl | isopropyl | 2-chloro-4-methylphenyl |
| CH₃CHCl | isopropyl | 2-chloro-5-methylphenyl |
| CH₃CHCl | isopropyl | 2-chloro-6-methylphenyl |
| CH₃CHCl | isopropyl | 3-chloro-4-methylphenyl |
| CH₃CHCl | isopropyl | 3-chloro-4-trifluoromethylphenyl |
| CH₃CHCl | isopropyl | 3-chloro-4-trifluromethoxyphenyl |
| CH₃CHCl | isopropyl | 3-chloro-4-trifluoromethylthiophenyl |
| CH₃CHCl | isopropyl | 2-bromophenyl |
| CH₃CHCl | isopropyl | 2-trifluoromethylphenyl |
| CH₃CHCl | isopropyl | 3-trifluoromethylphenyl |
| CH₃CHCl | isopropyl | 4-trifluoromethylphenyl |
| CH₃CHCl | isopropyl | 2-trifluromethoxyphenyl |
| CH₃CHCl | isopropyl | 2-difluromethoxyphenyl |
| CH₃CHCl | isopropyl | 2-(2,2,2-trifluoroethoxy)phenyl |
| CH₃CHCl | isopropyl | 2-(2,2,2-trifluoroethylthio)phenyl |
| CH₃CHCl | isopropyl | 2-trifluoromethylthiophenyl |
| CH₃CHCl | isopropyl | 2-methylphenyl |
| CH₃CHCl | isopropyl | 3-methylphenyl |
| CH₃CHCl | isopropyl | 4-methylphenyl |
| CH₃CHCl | isopropyl | 2,3-dimethylphenyl |
| CH₃CHCl | isopropyl | 2,4-dimethylphenyl |
| CH₃CHCl | isopropyl | 2,5-dimethylphenyl |
| CH₃CHCl | isopropyl | 2,6-dimethylphenyl |
| CH₃CHCl | isopropyl | 2,4,6-trimethylphenyl |
| CH₃CHCl | isopropyl | 2-ethylphenyl |
| CH₃CHCl | isopropyl | 3-ethylphenyl |
| CH₃CHCl | isopropyl | 4-ethylphenyl |
| CH₃CHCl | isopropyl | 2-methoxyphenyl |
| CH₃CHCl | isopropyl | 3-methoxyphenyl |
| CH₃CHCl | isopropyl | 4-methoxyphenyl |
| CH₃CHCl | isopropyl | 2-methylthiophenyl |
| CH₃CHCl | isopropyl | 2-nitrophenyl |
| CH₃CHCl | isopropyl | 2-cyanophenyl |
| CH₃CHBr | ethyl | ethyl |
| CH₃CHBr | ethyl | cyclohexyl |
| CH₃CHBr | n-propyl | n-propyl |
| CH₃CHBr | n-propyl | cyclopropyl |
| CH₃CHBr | n-propyl | cyclopentyl |
| CH₃CHBr | allyl | allyl |
| CH₃CHBr | propargyl | propargyl |
| CH₃CHBr | methyl | phenyl |
| CH₃CHBr | ethyl | phenyl |
| CH₃CHBr | n-propyl | phenyl |
| CH₃CHBr | isopropyl | phenyl |
| CH₃CHBr | n-butyl | phenyl |
| CH₃CHBr | s-butyl | phenyl |
| CH₃CHBr | isobutyl | phenyl |
| CH₃CHBr | phenyl | phenyl |
| CH₃CHBr | isopropyl | 2-fluorophenyl |
| CH₃CHBr | isopropyl | 3-fluorophenyl |
| CH₃CHBr | isopropyl | 4-fluorophenyl |
| CH₃CHBr | isopropyl | 2-chlorophenyl |
| CH₃CHBr | isopropyl | 3-chlorophenyl |
| CH₃CHBr | isopropyl | 4-chlorophenyl |
| CH₃CHBr | isopropyl | 2,3-dichlorophenyl |
| CH₃CHBr | isopropyl | 2,4-dichlorophenyl |
| CH₃CHBr | isopropyl | 2,5-dichlorophenyl |
| CH₃CHBr | isopropyl | 2,6-dichlorophenyl |
| CH₃CHBr | isopropyl | 3,4-dichlorophenyl |
| CH₃CHBr | isopropyl | 3,5-dichlorophenyl |
| CH₃CHBr | isopropyl | 2,4,6-trichlorophenyl |
| CH₃CHBr | isopropyl | 2-chloro-3-methylphenyl |
| CH₃CHBr | isopropyl | 2-chloro-4-methylphenyl |
| CH₃CHBr | isopropyl | 2-chloro-5-methylphenyl |
| CH₃CHBr | isopropyl | 2-chloro-6-methylphenyl |
| CH₃CHBr | isopropyl | 3-chloro-4-methylphenyl |
| CH₃CHBr | isopropyl | 3-chloro-4-trifluoromethylphenyl |
| CH₃CHBr | isopropyl | 3-chloro-4-trifluromethoxyphenyl |
| CH₃CHBr | isopropyl | 3-chloro-4-trifluoromethylthiophenyl |
| CH₃CHBr | isopropyl | 2-bromophenyl |
| CH₃CHBr | isopropyl | 2-trifluoromethylphenyl |
| CH₃CHBr | isopropyl | 3-trifluoromethylphenyl |
| CH₃CHBr | isopropyl | 4-trifluoromethylphenyl |
| CH₃CHBr | isopropyl | 2-trifluromethoxyphenyl |
| CH₃CHBr | isopropyl | 2-difluoromethoxyphenyl |
| CH₃CHBr | isopropyl | 2-(2,2,2-trifluoroethoxy)phenyl |
| CH₃CHBr | isopropyl | 2-(2,2,2-trifluoroethylthio)phenyl |
| CH₃CHBr | isopropyl | 2-trifluoromethylthiophenyl |
| CH₃CHBr | isopropyl | 2-methylphenyl |
| CH₃CHBr | isopropyl | 3-methylphenyl |
| CH₃CHBr | isopropyl | 4-methylphenyl |
| CH₃CHBr | isopropyl | 2,3-dimethylphenyl |
| CH₃CHBr | isopropyl | 2,4-dimethylphenyl |
| CH₃CHBr | isopropyl | 2,5-dimethylphenyl |
| CH₃CHBr | isopropyl | 2,6-dimethylphenyl |
| CH₃CHBr | isopropyl | 2,4,6-trimethylphenyl |
| CH₃CHBr | isopropyl | 2-ethylphenyl |
| CH₃CHBr | isopropyl | 3-ethylphenyl |
| CH₃CHBr | isopropyl | 4-ethylphenyl |
| CH₃CHBr | isopropyl | 2-methoxyphenyl |
| CH₃CHBr | isopropyl | 3-methoxyphenyl |
| CH₃CHBr | isopropyl | 4-methoxyphenyl |
| CH₃CHBr | isopropyl | 2-methylthiophenyl |
| CH₃CHBr | isopropyl | 2-nitrophenyl |
| CH₃CHBr | isopropyl | 2-cyanophenyl |
| CH₃CHF | ethyl | ethyl |
| CH₃CHF | ethyl | cyclohexyl |
| CH₃CHF | n-propyl | n-propyl |
| CH₃CHF | n-propyl | cyclopropyl |
| CH₃CHF | n-propyl | cyclopentyl |
| CH₃CHF | allyl | allyl |
| CH₃CHF | propargyl | propargyl |
| CH₃CHF | methyl | phenyl |
| CH₃CHF | ethyl | phenyl |
| CH₃CHF | n-propyl | phenyl |
| CH₃CHF | isopropyl | phenyl |
| CH₃CHF | n-butyl | phenyl |
| CH₃CHF | s-butyl | phenyl |
| CH₃CHF | isobutyl | phenyl |
| CH₃CHF | phenyl | phenyl |
| CH₃CHF | isopropyl | 2-fluorophenyl |
| CH₃CHF | isopropyl | 3-fluorophenyl |
| CH₃CHF | isopropyl | 4-fluorophenyl |
| CH₃CHF | isopropyl | 2-chlorophenyl |
| CH₃CHF | isopropyl | 3-chlorophenyl |
| CH₃CHF | isopropyl | 4-chlorophenyl |
| CH₃CHF | isopropyl | 2,3-dichlorophenyl |
| CH₃CHF | isopropyl | 2,4-dichlorophenyl |
| CH₃CHF | isopropyl | 2,5-dichlorophenyl |
| CH₃CHF | isopropyl | 2,6-dichlorophenyl |
| CH₃CHF | isopropyl | 3,4-dichlorophenyl |
| CH₃CHF | isopropyl | 3,5-dichlorophenyl |
| CH₃CHF | isopropyl | 2,4,6-trichlorophenyl |
| CH₃CHF | isopropyl | 2-chloro-3-methylphenyl |
| CH₃CHF | isopropyl | 2-chloro-4-methylphenyl |
| CH₃CHF | isopropyl | 2-chloro-5-methylphenyl |
| CH₃CHF | isopropyl | 2-chloro-6-methylphenyl |
| CH₃CHF | isopropyl | 3-chloro-4-methylphenyl |
| CH₃CHF | isopropyl | 3-chloro-4-trifluoromethylphenyl |
| CH₃CHF | isopropyl | 3-chloro-4-trifluromethoxyphenyl |
| CH₃CHF | isopropyl | 3-chloro-4-trifluoromethylthiophenyl |
| CH₃CHF | isopropyl | 2-bromophenyl |
| CH₃CHF | isopropyl | 2-trifluoromethylphenyl |

TABLE 1-continued $$R^1-N(-C(=O)-)-N(-C(=O)-N(R^1)(R^3)) \text{ with } N=N$$

| R¹ | R² | R³ |
| --- | --- | --- |
| CH₃CHF | isopropyl | 3-trifluoromethylphenyl |
| CH₃CHF | isopropyl | 4-trifluoromethylphenyl |
| CH₃CHF | isopropyl | 2-trifluromethoxyphenyl |
| CH₃CHF | isopropyl | 2-difluoromethoxyphenyl |
| CH₃CHF | isopropyl | 2-(2,2,2-trifluoroethoxy)phenyl |
| CH₃CHF | isopropyl | 2-(2,2,2-trifluoroethylthio)phenyl |
| CH₃CHF | isopropyl | 2-trifluoromethylthiophenyl |
| CH₃CHF | isopropyl | 2-methylphenyl |
| CH₃CHF | isopropyl | 3-methylphenyl |
| CH₃CHF | isopropyl | 4-methylphenyl |
| CH₃CHF | isopropyl | 2,3-dimethylphenyl |
| CH₃CHF | isopropyl | 2,4-dimethylphenyl |
| CH₃CHF | isopropyl | 2,5-dimethylphenyl |
| CH₃CHF | isopropyl | 2,6-dimethylphenyl |
| CH₃CHF | isopropyl | 2,4,6-trimethylphenyl |
| CH₃CHF | isopropyl | 2-ethylphenyl |
| CH₃CHF | isopropyl | 3-ethylphenyl |
| CH₃CHF | isopropyl | 4-ethylphenyl |
| CH₃CHF | isopropyl | 2-methoxyphenyl |
| CH₃CHF | isopropyl | 3-methoxyphenyl |
| CH₃CHF | isopropyl | 4-methoxyphenyl |
| CH₃CHF | isopropyl | 2-methylthiophenyl |
| CH₃CHF | isopropyl | 2-nitrophenyl |
| CH₃CHF | isopropyl | 2-cyanophenyl |
| ClCH₂CH₂ | ethyl | ethyl |
| ClCH₂CH₂ | ethyl | cyclohexyl |
| ClCH₂CH₂ | n-propyl | n-propyl |
| ClCH₂CH₂ | n-propyl | cyclopropyl |
| ClCH₂CH₂ | n-propyl | cyclopentyl |
| ClCH₂CH₂ | allyl | allyl |
| ClCH₂CH₂ | propargyl | propargyl |
| ClCH₂CH₂ | methyl | phenyl |
| ClCH₂CH₂ | ethyl | phenyl |
| ClCH₂CH₂ | n-propyl | phenyl |
| ClCH₂CH₂ | isopropyl | phenyl |
| ClCH₂CH₂ | n-butyl | phenyl |
| ClCH₂CH₂ | s-butyl | phenyl |
| ClCH₂CH₂ | isobutyl | phenyl |
| ClCH₂CH₂ | phenyl | phenyl |
| ClCH₂CH₂ | isopropyl | 2-fluorophenyl |
| ClCH₂CH₂ | isopropyl | 3-fluorophenyl |
| ClCH₂CH₂ | isopropyl | 4-fluorophenyl |
| ClCH₂CH₂ | isopropyl | 2-chlorophenyl |
| ClCH₂CH₂ | isopropyl | 3-chlorophenyl |
| ClCH₂CH₂ | isopropyl | 4-chlorophenyl |
| ClCH₂CH₂ | isopropyl | 2,3-dichlorophenyl |
| ClCH₂CH₂ | isopropyl | 2,4-dichlorophenyl |
| ClCH₂CH₂ | isopropyl | 2,5-dichlorophenyl |
| ClCH₂CH₂ | isopropyl | 2,6-dichlorophenyl |
| ClCH₂CH₂ | isopropyl | 3,4-dichlorophenyl |
| ClCH₂CH₂ | isopropyl | 3,5-dichlorophenyl |
| ClCH₂CH₂ | isopropyl | 2,4,6-trichlorophenyl |
| ClCH₂CH₂ | isopropyl | 2-chloro-3-methylphenyl |
| ClCH₂CH₂ | isopropyl | 2-chloro-4-methylphenyl |
| ClCH₂CH₂ | isopropyl | 2-chloro-5-methylphenyl |
| ClCH₂CH₂ | isopropyl | 2-chloro-6-methylphenyl |
| ClCH₂CH₂ | isopropyl | 3-chloro-4-methylphenyl |
| ClCH₂CH₂ | isopropyl | 3-chloro-4-trifluoromethylphenyl |
| ClCH₂CH₂ | isopropyl | 3-chloro-4-trifluromethoxyphenyl |
| ClCH₂CH₂ | isopropyl | 3-chloro-4-trifluoromethylthiophenyl |
| ClCH₂CH₂ | isopropyl | 2-bromophenyl |
| ClCH₂CH₂ | isopropyl | 2-trifluoromethylphenyl |
| ClCH₂CH₂ | isopropyl | 3-trifluoromethylphenyl |
| ClCH₂CH₂ | isopropyl | 4-trifluoromethylphenyl |
| ClCH₂CH₂ | isopropyl | 2-trifluromethoxyphenyl |
| ClCH₂CH₂ | isopropyl | 2-difluoromethoxyphenyl |
| ClCH₂CH₂ | isopropyl | 2-(2,2,2-trifluoroethoxy)phenyl |
| ClCH₂CH₂ | isopropyl | 2-(2,2,2-trifluoroethylthio)phenyl |
| ClCH₂CH₂ | isopropyl | 2-trifluoromethylthiophenyl |
| ClCH₂CH₂ | isopropyl | 2-methylphenyl |
| ClCH₂CH₂ | isopropyl | 3-methylphenyl |
| ClCH₂CH₂ | isopropyl | 4-methylphenyl |
| ClCH₂CH₂ | isopropyl | 2,3-dimethylphenyl |
| ClCH₂CH₂ | isopropyl | 2,4-dimethylphenyl |
| ClCH₂CH₂ | isopropyl | 2,5-dimethylphenyl |
| ClCH₂CH₂ | isopropyl | 2,6-dimethylphenyl |
| ClCH₂CH₂ | isopropyl | 2,4,6-trimethylphenyl |
| ClCH₂CH₂ | isopropyl | 2-ethylphenyl |
| ClCH₂CH₂ | isopropyl | 3-ethylphenyl |
| ClCH₂CH₂ | isopropyl | 4-ethylphenyl |
| ClCH₂CH₂ | isopropyl | 2-methoxyphenyl |
| ClCH₂CH₂ | isopropyl | 3-methoxyphenyl |
| ClCH₂CH₂ | isopropyl | 4-methoxyphenyl |
| ClCH₂CH₂ | isopropyl | 2-methylthiophenyl |
| ClCH₂CH₂ | isopropyl | 2-nitrophenyl |
| ClCH₂CH₂ | isopropyl | 2-cyanophenyl |
| BrCH₂CH₂ | ethyl | ethyl |
| BrCH₂CH₂ | ethyl | cyclohexyl |
| BrCH₂CH₂ | n-propyl | n-propyl |
| BrCH₂CH₂ | n-propyl | cyclopropyl |
| BrCH₂CH₂ | n-propyl | cyclopentyl |
| BrCH₂CH₂ | allyl | allyl |
| BrCH₂CH₂ | propargyl | propargyl |
| BrCH₂CH₂ | methyl | phenyl |
| BrCH₂CH₂ | ethyl | phenyl |
| BrCH₂CH₂ | n-propyl | phenyl |
| BrCH₂CH₂ | isopropyl | phenyl |
| BrCH₂CH₂ | n-butyl | phenyl |
| BrCH₂CH₂ | s-butyl | phenyl |
| BrCH₂CH₂ | isobutyl | phenyl |
| BrCH₂CH₂ | phenyl | phenyl |
| BrCH₂CH₂ | isopropyl | 2-fluorophenyl |
| BrCH₂CH₂ | isopropyl | 3-fluorophenyl |
| BrCH₂CH₂ | isopropyl | 4-fluorophenyl |
| BrCH₂CH₂ | isopropyl | 2-chlorophenyl |
| BrCH₂CH₂ | isopropyl | 3-chlorophenyl |
| BrCH₂CH₂ | isopropyl | 4-chlorophenyl |
| BrCH₂CH₂ | isopropyl | 2,3-dichlorophenyl |
| BrCH₂CH₂ | isopropyl | 2,4-dichlorophenyl |
| BrCH₂CH₂ | isopropyl | 2,5-dichlorophenyl |
| BrCH₂CH₂ | isopropyl | 2,6-dichlorophenyl |
| BrCH₂CH₂ | isopropyl | 3,4-dichlorophenyl |
| BrCH₂CH₂ | isopropyl | 3,5-dichlorophenyl |
| BrCH₂CH₂ | isopropyl | 2,4,6-trichlorophenyl |
| BrCH₂CH₂ | isopropyl | 2-chloro-3-methylphenyl |
| BrCH₂CH₂ | isopropyl | 2-chloro-4-methylphenyl |
| BrCH₂CH₂ | isopropyl | 2-chloro-5-methylphenyl |
| BrCH₂CH₂ | isopropyl | 2-chloro-6-methylphenyl |
| BrCH₂CH₂ | isopropyl | 3-chloro-4-methylphenyl |
| BrCH₂CH₂ | isopropyl | 3-chloro-4-trifluoromethylphenyl |
| BrCH₂CH₂ | isopropyl | 3-chloro-4-trifluromethoxyphenyl |
| BrCH₂CH₂ | isopropyl | 3-chloro-4-trifluoromethylthiophenyl |
| BrCH₂CH₂ | isopropyl | 2-bromophenyl |
| BrCH₂CH₂ | isopropyl | 2-trifluoromethylphenyl |
| BrCH₂CH₂ | isopropyl | 3-trifluoromethylphenyl |
| BrCH₂CH₂ | isopropyl | 4-trifluoromethylphenyl |
| BrCH₂CH₂ | isopropyl | 2-trifluromethoxyphenyl |
| BrCH₂CH₂ | isopropyl | 2-difluoromethoxyphenyl |
| BrCH₂CH₂ | isopropyl | 2-(2,2,2-trifluoroethoxy)phenyl |
| BrCH₂CH₂ | isopropyl | 2-(2,2,2-trifluoroethylthio)phenyl |
| BrCH₂CH₂ | isopropyl | 2-trifluoromethylthiophenyl |
| BrCH₂CH₂ | isopropyl | 2-methylphenyl |
| BrCH₂CH₂ | isopropyl | 3-methylphenyl |
| BrCH₂CH₂ | isopropyl | 4-methylphenyl |
| BrCH₂CH₂ | isopropyl | 2,3-dimethylphenyl |
| BrCH₂CH₂ | isopropyl | 2,4-dimethylphenyl |
| BrCH₂CH₂ | isopropyl | 2,5-dimethylphenyl |
| BrCH₂CH₂ | isopropyl | 2,6-dimethylphenyl |
| BrCH₂CH₂ | isopropyl | 2,4,6-trimethylphenyl |
| BrCH₂CH₂ | isopropyl | 2-ethylphenyl |

TABLE 1-continued

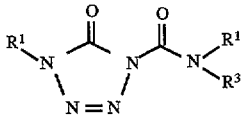

| R¹ | R² | R³ |
|---|---|---|
| BrCH₂CH₂ | isopropyl | 3-ethylphenyl |
| BrCH₂CH₂ | isopropyl | 4-ethylphenyl |
| BrCH₂CH₂ | isopropyl | 2-methoxyphenyl |
| BrCH₂CH₂ | isopropyl | 3-methoxyphenyl |
| BrCH₂CH₂ | isopropyl | 4-methoxyphenyl |
| BrCH₂CH₂ | isopropyl | 2-methylthiophenyl |
| BrCH₂CH₂ | isopropyl | 2-nitrophenyl |
| BrCH₂CH₂ | isopropyl | 2-cyanophenyl |
| FCH₂CH₂ | ethyl | ethyl |
| FCH₂CH₂ | ethyl | cyclohexyl |
| FCH₂CH₂ | n-propyl | n-propyl |
| FCH₂CH₂ | n-propyl | cyclopropyl |
| FCH₂CH₂ | n-propyl | cyclopentyl |
| FCH₂CH₂ | allyl | allyl |
| FCH₂CH₂ | propargyl | propargyl |
| FCH₂CH₂ | methyl | phenyl |
| FCH₂CH₂ | ethyl | phenyl |
| FCH₂CH₂ | n-propyl | phenyl |
| FCH₂CH₂ | isopropyl | phenyl |
| FCH₂CH₂ | n-butyl | phenyl |
| FCH₂CH₂ | s-butyl | phenyl |
| FCH₂CH₂ | isobutyl | phenyl |
| FCH₂CH₂ | phenyl | phenyl |
| FCH₂CH₂ | isopropyl | 2-fluorophenyl |
| FCH₂CH₂ | isopropyl | 3-fluorophenyl |
| FCH₂CH₂ | isopropyl | 4-fluorophenyl |
| FCH₂CH₂ | isopropyl | 2-chlorophenyl |
| FCH₂CH₂ | isopropyl | 3-chlorophenyl |
| FCH₂CH₂ | isopropyl | 4-chlorophenyl |
| FCH₂CH₂ | isopropyl | 2,3-dichlorophenyl |
| FCH₂CH₂ | isopropyl | 2,4-dichlorophenyl |
| FCH₂CH₂ | isopropyl | 2,5-dichlorophenyl |
| FCH₂CH₂ | isopropyl | 2,6-dichlorophenyl |
| FCH₂CH₂ | isopropyl | 3,4-dichlorophenyl |
| FCH₂CH₂ | isopropyl | 3,5-dichlorophenyl |
| FCH₂CH₂ | isopropyl | 2,4,6-trichlorophenyl |
| FCH₂CH₂ | isopropyl | 2-chloro-3-methylphenyl |
| FCH₂CH₂ | isopropyl | 2-chloro-4-methylphenyl |
| FCH₂CH₂ | isopropyl | 2-chloro-5-methylphenyl |
| FCH₂CH₂ | isopropyl | 2-chloro-6-methylphenyl |
| FCH₂CH₂ | isopropyl | 3-chloro-4-methylphenyl |
| FCH₂CH₂ | isopropyl | 3-chloro-4-trifluoromethylphenyl |
| FCH₂CH₂ | isopropyl | 3-chloro-4-trifluromethoxyphenyl |
| FCH₂CH₂ | isopropyl | 3-chloro-4-trifluoromethylthiophenyl |
| FCH₂CH₂ | isopropyl | 2-bromophenyl |
| FCH₂CH₂ | isopropyl | 2-trifluoromethylphenyl |
| FCH₂CH₂ | isopropyl | 3-trifluoromethylphenyl |
| FCH₂CH₂ | isopropyl | 4-trifluoromethylphenyl |
| FCH₂CH₂ | isopropyl | 2-trifluromethoxyphenyl |
| FCH₂CH₂ | isopropyl | 2-difluoromethoxyphenyl |
| FCH₂CH₂ | isopropyl | 2-(2,2,2-trifluoroethoxy)phenyl |
| FCH₂CH₂ | isopropyl | 2-(2,2,2-trifluoroethylthio)phenyl |
| FCH₂CH₂ | isopropyl | 2-trifluoromethylthiophenyl |
| FCH₂CH₂ | isopropyl | 2-methylphenyl |
| FCH₂CH₂ | isopropyl | 3-methylphenyl |
| FCH₂CH₂ | isopropyl | 4-methylphenyl |
| FCH₂CH₂ | isopropyl | 2,3-dimethylphenyl |
| FCH₂CH₂ | isopropyl | 2,4-dimethylphenyl |
| FCH₂CH₂ | isopropyl | 2,5-dimethylphenyl |
| FCH₂CH₂ | isopropyl | 2,6-dimethylphenyl |
| FCH₂CH₂ | isopropyl | 2,4,6-trimethylphenyl |
| FCH₂CH₂ | isopropyl | 2-ethylphenyl |
| FCH₂CH₂ | isopropyl | 3-ethylphenyl |
| FCH₂CH₂ | isopropyl | 4-ethylphenyl |
| FCH₂CH₂ | isopropyl | 2-methoxyphenyl |
| FCH₂CH₂ | isopropyl | 3-methoxyphenyl |
| FCH₂CH₂ | isopropyl | 4-methoxyphenyl |
| FCH₂CH₂ | isopropyl | 2-methylthiophenyl |
| FCH₂CH₂ | isopropyl | 2-nitrophenyl |
| FCH₂CH₂ | isopropyl | 2-cyanophenyl |

TABLE 1-continued

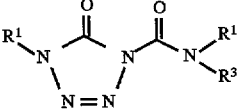

| R¹ | R² | R³ |
|---|---|---|
| CH₃CCl₂ | ethyl | ethyl |
| CH₃CCl₂ | ethyl | cyclohexyl |
| CH₃CCl₂ | n-propyl | n-propyl |
| CH₃CCl₂ | n-propyl | cyclopropyl |
| CH₃CCl₂ | n-propyl | cyclopentyl |
| CH₃CCl₂ | allyl | allyl |
| CH₃CCl₂ | propargyl | propargyl |
| CH₃CCl₂ | methyl | phenyl |
| CH₃CCl₂ | ethyl | phenyl |
| CH₃CCl₂ | n-propyl | phenyl |
| CH₃CCl₂ | isopropyl | phenyl |
| CH₃CCl₂ | n-butyl | phenyl |
| CH₃CCl₂ | s-butyl | phenyl |
| CH₃CCl₂ | isobutyl | phenyl |
| CH₃CCl₂ | phenyl | phenyl |
| CH₃CCl₂ | isopropyl | 2-fluorophenyl |
| CH₃CCl₂ | isopropyl | 3-fluorophenyl |
| CH₃CCl₂ | isopropyl | 4-fluorophenyl |
| CH₃CCl₂ | isopropyl | 2-chlorophenyl |
| CH₃CCl₂ | isopropyl | 3-chlorophenyl |
| CH₃CCl₂ | isopropyl | 4-chlorophenyl |
| CH₃CCl₂ | isopropyl | 2,3-dichlorophenyl |
| CH₃CCl₂ | isopropyl | 2,4-dichlorophenyl |
| CH₃CCl₂ | isopropyl | 2,5-dichlorophenyl |
| CH₃CCl₂ | isopropyl | 2,6-dichlorophenyl |
| CH₃CCl₂ | isopropyl | 3,4-dichlorophenyl |
| CH₃CCl₂ | isopropyl | 3,5-dichlorophenyl |
| CH₃CCl₂ | isopropyl | 2,4,6-trichlorophenyl |
| CH₃CCl₂ | isopropyl | 2-chloro-3-methylphenyl |
| CH₃CCl₂ | isopropyl | 2-chloro-4-methylphenyl |
| CH₃CCl₂ | isopropyl | 2-chloro-5-methylphenyl |
| CH₃CCl₂ | isopropyl | 2-chloro-6-methylphenyl |
| CH₃CCl₂ | isopropyl | 3-chloro-4-methylphenyl |
| CH₃CCl₂ | isopropyl | 3-chloro-4-trifluoromethylphenyl |
| CH₃CCl₂ | isopropyl | 3-chloro-4-trifluromethoxyphenyl |
| CH₃CCl₂ | isopropyl | 3-chloro-4-trifluoromethylthiophenyl |
| CH₃CCl₂ | isopropyl | 2-bromophenyl |
| CH₃CCl₂ | isopropyl | 2-trifluoromethylphenyl |
| CH₃CCl₂ | isopropyl | 3-trifluoromethylphenyl |
| CH₃CCl₂ | isopropyl | 4-trifluoromethylphenyl |
| CH₃CCl₂ | isopropyl | 2-trifluromethoxyphenyl |
| CH₃CCl₂ | isopropyl | 2-difluoromethoxyphenyl |
| CH₃CCl₂ | isopropyl | 2-(2,2,2-trifluoroethoxy)phenyl |
| CH₃CCl₂ | isopropyl | 2-(2,2,2-trifluoroethylthio)phenyl |
| CH₃CCl₂ | isopropyl | 2-trifluoromethylthiophenyl |
| CH₃CCl₂ | isopropyl | 2-methylphenyl |
| CH₃CCl₂ | isopropyl | 3-methylphenyl |
| CH₃CCl₂ | isopropyl | 4-methylphenyl |
| CH₃CCl₂ | isopropyl | 2,3-dimethylphenyl |
| CH₃CCl₂ | isopropyl | 2,4-dimethylphenyl |
| CH₃CCl₂ | isopropyl | 2,5-dimethylphenyl |
| CH₃CCl₂ | isopropyl | 2,6-dimethylphenyl |
| CH₃CCl₂ | isopropyl | 2,4,6-trimethylphenyl |
| CH₃CCl₂ | isopropyl | 2-ethylphenyl |
| CH₃CCl₂ | isopropyl | 3-ethylphenyl |
| CH₃CCl₂ | isopropyl | 4-ethylphenyl |
| CH₃CCl₂ | isopropyl | 2-methoxyphenyl |
| CH₃CCl₂ | isopropyl | 3-methoxyphenyl |
| CH₃CCl₂ | isopropyl | 4-methoxyphenyl |
| CH₃CCl₂ | isopropyl | 2-methylthiophenyl |
| CH₃CCl₂ | isopropyl | 2-nitrophenyl |
| CH₃CCl₂ | isopropyl | 2-cyanophenyl |
| ClCH₂CHCl | ethyl | ethyl |
| ClCH₂CHCl | ethyl | cyclohexyl |
| ClCH₂CHCl | n-propyl | n-propyl |
| ClCH₂CHCl | n-propyl | cyclopropyl |
| ClCH₂CHCl | n-propyl | cyclopentyl |
| ClCH₂CHCl | allyl | allyl |
| ClCH₂CHCl | propargyl | propargyl |
| ClCH₂CHCl | methyl | phenyl |

TABLE 1-continued $$\underset{N=N}{R^1-N}\overset{O}{\underset{}{\parallel}}\overset{O}{\underset{R^3}{\parallel}}R^1$$

| R¹ | R² | R³ |
| --- | --- | --- |
| ClCH₂CHCl | ethyl | phenyl |
| ClCH₂CHCl | n-propyl | phenyl |
| ClCH₂CHCl | isopropyl | phenyl |
| ClCH₂CHCl | n-butyl | phenyl |
| ClCH₂CHCl | s-butyl | phenyl |
| ClCH₂CHCl | isobutyl | phenyl |
| ClCH₂CHCl | phenyl | phenyl |
| ClCH₂CHCl | isopropyl | 2-fluorophenyl |
| ClCH₂CHCl | isopropyl | 3-fluorophenyl |
| ClCH₂CHCl | isopropyl | 4-fluorophenyl |
| ClCH₂CHCl | isopropyl | 2-chlorophenyl |
| ClCH₂CHCl | isopropyl | 3-chlorophenyl |
| ClCH₂CHCl | isopropyl | 4-chlorophenyl |
| ClCH₂CHCl | isopropyl | 2,3-dichlorophenyl |
| ClCH₂CHCl | isopropyl | 2,4-dichlorophenyl |
| ClCH₂CHCl | isopropyl | 2,5-dichlorophenyl |
| ClCH₂CHCl | isopropyl | 2,6-dichlorophenyl |
| ClCH₂CHCl | isopropyl | 3,4-dichlorophenyl |
| ClCH₂CHCl | isopropyl | 3,5-dichlorophenyl |
| ClCH₂CHCl | isopropyl | 2,4,6-trichlorophenyl |
| ClCH₂CHCl | isopropyl | 2-chloro-3-methylphenyl |
| ClCH₂CHCl | isopropyl | 2-chloro-4-methylphenyl |
| ClCH₂CHCl | isopropyl | 2-chloro-5-methylphenyl |
| ClCH₂CHCl | isopropyl | 2-chloro-6-methylphenyl |
| ClCH₂CHCl | isopropyl | 3-chloro-4-methylphenyl |
| ClCH₂CHCl | isopropyl | 3-chloro-4-trifluoromethylphenyl |
| ClCH₂CHCl | isopropyl | 3-chloro-4-trifluromethoxyphenyl |
| ClCH₂CHCl | isopropyl | 3-chloro-4-trifluoromethylthiophenyl |
| ClCH₂CHCl | isopropyl | 2-bromophenyl |
| ClCH₂CHCl | isopropyl | 2-trifluoromethylphenyl |
| ClCH₂CHCl | isopropyl | 3-trifluoromethylphenyl |
| ClCH₂CHCl | isopropyl | 4-trifluoromethylphenyl |
| ClCH₂CHCl | isopropyl | 2-trifluromethoxyphenyl |
| ClCH₂CHCl | isopropyl | 2-difluoromethoxyphenyl |
| ClCH₂CHCl | isopropyl | 2-(2,2,2-trifluoroethoxy)phenyl |
| ClCH₂CHCl | isopropyl | 2-(2,2,2-trifluoroethylthio)phenyl |
| ClCH₂CHCl | isopropyl | 2-trifluoromethylthiophenyl |
| ClCH₂CHCl | isopropyl | 2-methylphenyl |
| ClCH₂CHCl | isopropyl | 3-methylphenyl |
| ClCH₂CHCl | isopropyl | 4-methylphenyl |
| ClCH₂CHCl | isopropyl | 2,3-dimethylphenyl |
| ClCH₂CHCl | isopropyl | 2,4-dimethylphenyl |
| ClCH₂CHCl | isopropyl | 2,5-dimethylphenyl |
| ClCH₂CHCl | isopropyl | 2,6-dimethylphenyl |
| ClCH₂CHCl | isopropyl | 2,4,6-trimethylphenyl |
| ClCH₂CHCl | isopropyl | 2-ethylphenyl |
| ClCH₂CHCl | isopropyl | 3-ethylphenyl |
| ClCH₂CHCl | isopropyl | 4-ethylphenyl |
| ClCH₂CHCl | isopropyl | 2-methoxyphenyl |
| ClCH₂CHCl | isopropyl | 3-methoxyphenyl |
| ClCH₂CHCl | isopropyl | 4-methoxyphenyl |
| ClCH₂CHCl | isopropyl | 2-methylthiophenyl |
| ClCH₂CHCl | isopropyl | 2-nitrophenyl |
| ClCH₂CHCl | isopropyl | 2-cyanophenyl |
| BrCH₂CHBr | ethyl | ethyl |
| BrCH₂CHBr | ethyl | cyclohexyl |
| BrCH₂CHBr | n-propyl | n-propyl |
| BrCH₂CHBr | n-propyl | cyclopropyl |
| BrCH₂CHBr | n-propyl | cyclopentyl |
| BrCH₂CHBr | allyl | allyl |
| BrCH₂CHBr | propargyl | propargyl |
| BrCH₂CHBr | methyl | phenyl |
| BrCH₂CHBr | ethyl | phenyl |
| BrCH₂CHBr | n-propyl | phenyl |
| BrCH₂CHBr | isopropyl | phenyl |
| BrCH₂CHBr | n-butyl | phenyl |
| BrCH₂CHBr | s-butyl | phenyl |
| BrCH₂CHBr | isobutyl | phenyl |
| BrCH₂CHBr | phenyl | phenyl |
| BrCH₂CHBr | isopropyl | 2-fluorophenyl |
| BrCH₂CHBr | isopropyl | 3-fluorophenyl |
| BrCH₂CHBr | isopropyl | 4-fluorophenyl |
| BrCH₂CHBr | isopropyl | 2-chlorophenyl |
| BrCH₂CHBr | isopropyl | 3-chlorophenyl |
| BrCH₂CHBr | isopropyl | 4-chlorophenyl |
| BrCH₂CHBr | isopropyl | 2,3-dichlorophenyl |
| BrCH₂CHBr | isopropyl | 2,4-dichlorophenyl |
| BrCH₂CHBr | isopropyl | 2,5-dichlorophenyl |
| BrCH₂CHBr | isopropyl | 2,6-dichlorophenyl |
| BrCH₂CHBr | isopropyl | 3,4-dichlorophenyl |
| BrCH₂CHBr | isopropyl | 3,5-dichlorophenyl |
| BrCH₂CHBr | isopropyl | 2,4,6-trichlorophenyl |
| BrCH₂CHBr | isopropyl | 2-chloro-3-methylphenyl |
| BrCH₂CHBr | isopropyl | 2-chloro-4-methylphenyl |
| BrCH₂CHBr | isopropyl | 2-chloro-5-methylphenyl |
| BrCH₂CHBr | isopropyl | 2-chloro-6-methylphenyl |
| BrCH₂CHBr | isopropyl | 3-chloro-4-methylphenyl |
| BrCH₂CHBr | isopropyl | 3-chloro-4-trifluoromethylphenyl |
| BrCH₂CHBr | isopropyl | 3-chloro-4-trifluromethoxyphenyl |
| BrCH₂CHBr | isopropyl | 3-chloro-4-trifluoromethylthiophenyl |
| BrCH₂CHBr | isopropyl | 2-bromophenyl |
| BrCH₂CHBr | isopropyl | 2-trifluoromethylphenyl |
| BrCH₂CHBr | isopropyl | 3-trifluoromethylphenyl |
| BrCH₂CHBr | isopropyl | 4-trifluoromethylphenyl |
| BrCH₂CHBr | isopropyl | 2-trifluoromethoxyphenyl |
| BrCH₂CHBr | isopropyl | 2-difluoromethoxyphenyl |
| BrCH₂CHBr | isopropyl | 2-(2,2,2-trifluoroethoxy)phenyl |
| BrCH₂CHBr | isopropyl | 2-(2,2,2-trifluoroethylthio)phenyl |
| BrCH₂CHBr | isopropyl | 2-trifluoromethylthiophenyl |
| BrCH₂CHBr | isopropyl | 2-methylphenyl |
| BrCH₂CHBr | isopropyl | 3-methylphenyl |
| BrCH₂CHBr | isopropyl | 4-methylphenyl |
| BrCH₂CHBr | isopropyl | 2,3-dimethylphenyl |
| BrCH₂CHBr | isopropyl | 2,4-dimethylphenyl |
| BrCH₂CHBr | isopropyl | 2,5-dimethylphenyl |
| BrCH₂CHBr | isopropyl | 2,6-dimethylphenyl |
| BrCH₂CHBr | isopropyl | 2,4,6-trimethylphenyl |
| BrCH₂CHBr | isopropyl | 2-ethylphenyl |
| BrCH₂CHBr | isopropyl | 3-ethylphenyl |
| BrCH₂CHBr | isopropyl | 4-ethylphenyl |
| BrCH₂CHBr | isopropyl | 2-methoxyphenyl |
| BrCH₂CHBr | isopropyl | 3-methoxyphenyl |
| BrCH₂CHBr | isopropyl | 4-methoxyphenyl |
| BrCH₂CHBr | isopropyl | 2-methylthiophenyl |
| BrCH₂CHBr | isopropyl | 2-nitrophenyl |
| BrCH₂CHBr | isopropyl | 2-cyanophenyl |
| FCH₂CHF | ethyl | ethyl |
| FCH₂CHF | ethyl | cyclohexyl |
| FCH₂CHF | n-propyl | n-propyl |
| FCH₂CHF | n-propyl | cyclopropyl |
| FCH₂CHF | n-propyl | cyclopentyl |
| FCH₂CHF | allyl | allyl |
| FCH₂CHF | propargyl | propargyl |
| FCH₂CHF | methyl | phenyl |
| FCH₂CHF | ethyl | phenyl |
| FCH₂CHF | n-propyl | phenyl |
| FCH₂CHF | isopropyl | phenyl |
| FCH₂CHF | n-butyl | phenyl |
| FCH₂CHF | s-butyl | phenyl |
| FCH₂CHF | isobutyl | phenyl |
| FCH₂CHF | phenyl | phenyl |
| FCH₂CHF | isopropyl | 2-fluorophenyl |
| FCH₂CHF | isopropyl | 3-fluorophenyl |
| FCH₂CHF | isopropyl | 4-fluorophenyl |
| FCH₂CHF | isopropyl | 2-chlorophenyl |
| FCH₂CHF | isopropyl | 3-chlorophenyl |
| FCH₂CHF | isopropyl | 4-chlorophenyl |
| FCH₂CHF | isopropyl | 2,3-dichlorophenyl |
| FCH₂CHF | isopropyl | 2,4-dichlorophenyl |
| FCH₂CHF | isopropyl | 2,5-dichlorophenyl |

TABLE 1-continued

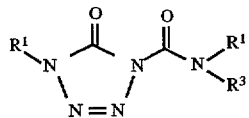

| R¹ | R² | R³ |
|---|---|---|
| FCH₂CHF | isopropyl | 2,6-dichlorophenyl |
| FCH₂CHF | isopropyl | 3,4-dichlorophenyl |
| FCH₂CHF | isopropyl | 3,5-dichlorophenyl |
| FCH₂CHF | isopropyl | 2,4,6-trichlorophenyl |
| FCH₂CHF | isopropyl | 2-chloro-3-methylphenyl |
| FCH₂CHF | isopropyl | 2-chloro-4-methylphenyl |
| FCH₂CHF | isopropyl | 2-chloro-5-methylphenyl |
| FCH₂CHF | isopropyl | 2-chloro-6-methylphenyl |
| FCH₂CHF | isopropyl | 3-chloro-4-methylphenyl |
| FCH₂CHF | isopropyl | 3-chloro-4-trifluoromethylphenyl |
| FCH₂CHF | isopropyl | 3-chloro-4-trifluromethoxyphenyl |
| FCH₂CHF | isopropyl | 3-chloro-4-trifluoromethylthiophenyl |
| FCH₂CHF | isopropyl | 2-bromophenyl |
| FCH₂CHF | isopropyl | 2-trifluoromethylphenyl |
| FCH₂CHF | isopropyl | 3-trifluoromethylphenyl |
| FCH₂CHF | isopropyl | 4-trifluoromethylphenyl |
| FCH₂CHF | isopropyl | 2-trifluromethoxyphenyl |
| FCH₂CHF | isopropyl | 2-difluoromethoxyphenyl |
| FCH₂CHF | isopropyl | 2-(2,2,2-trifluoroethoxy)phenyl |
| FCH₂CHF | isopropyl | 2-(2,2,2-trifluoroethylthio)phenyl |
| FCH₂CHF | isopropyl | 2-trifluoromethylthiophenyl |
| FCH₂CHF | isopropyl | 2-methylphenyl |
| FCH₂CHF | isopropyl | 3-methylphenyl |
| FCH₂CHF | isopropyl | 4-methylphenyl |
| FCH₂CHF | isopropyl | 2,3-dimethylphenyl |
| FCH₂CHF | isopropyl | 2,4-dimethylphenyl |
| FCH₂CHF | isopropyl | 2,5-dimethylphenyl |
| FCH₂CHF | isopropyl | 2,6-dimethylphenyl |
| FCH₂CHF | isopropyl | 2,4,6-trimethylphenyl |
| FCH₂CHF | isopropyl | 2-ethylphenyl |
| FCH₂CHF | isopropyl | 3-ethylphenyl |
| FCH₂CHF | isopropyl | 4-ethylphenyl |
| FCH₂CHF | isopropyl | 2-methoxyphenyl |
| FCH₂CHF | isopropyl | 3-methoxyphenyl |
| FCH₂CHF | isopropyl | 4-methoxyphenyl |
| FCH₂CHF | isopropyl | 2-methylthiophenyl |
| FCH₂CHF | isopropyl | 2-nitrophenyl |
| FCH₂CHF | isopropyl | 2-cyanophenyl |
| CCl₃CH₂ | ethyl | ethyl |
| CCl₃CH₂ | ethyl | cyclohexyl |
| CCl₃CH₂ | n-propyl | n-propyl |
| CCl₃CH₂ | n-propyl | cyclopropyl |
| CCl₃CH₂ | n-propyl | cyclopentyl |
| CCl₃CH₂ | allyl | allyl |
| CCl₃CH₂ | propargyl | propargyl |
| CCl₃CH₂ | methyl | phenyl |
| CCl₃CH₂ | ethyl | phenyl |
| CCl₃CH₂ | n-propyl | phenyl |
| CCl₃CH₂ | isopropyl | phenyl |
| CCl₃CH₂ | n-butyl | phenyl |
| CCl₃CH₂ | s-butyl | phenyl |
| CCl₃CH₂ | isobutyl | phenyl |
| CCl₃CH₂ | phenyl | phenyl |
| CCl₃CH₂ | isopropyl | 2-fluorophenyl |
| CCl₃CH₂ | isopropyl | 3-fluorophenyl |
| CCl₃CH₂ | isopropyl | 4-fluorophenyl |
| CCl₃CH₂ | isopropyl | 2-chlorophenyl |
| CCl₃CH₂ | isopropyl | 3-chlorophenyl |
| CCl₃CH₂ | isopropyl | 4-chlorophenyl |
| CCl₃CH₂ | isopropyl | 2,3-dichlorophenyl |
| CCl₃CH₂ | isopropyl | 2,4-dichlorophenyl |
| CCl₃CH₂ | isopropyl | 2,5-dichlorophenyl |
| CCl₃CH₂ | isopropyl | 2,6-dichlorophenyl |
| CCl₃CH₂ | isopropyl | 3,4-dichlorophenyl |
| CCl₃CH₂ | isopropyl | 3,5-dichlorophenyl |
| CCl₃CH₂ | isopropyl | 2,4,6-trichlorophenyl |
| CCl₃CH₂ | isopropyl | 2-chloro-3-methylphenyl |
| CCl₃CH₂ | isopropyl | 2-chloro-4-methylphenyl |
| CCl₃CH₂ | isopropyl | 2-chloro-5-methylphenyl |
| CCl₃CH₂ | isopropyl | 2-chloro-6-methylphenyl |

TABLE 1-continued

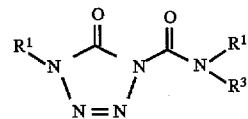

| R¹ | R² | R³ |
|---|---|---|
| CCl₃CH₂ | isopropyl | 3-chloro-4-methylphenyl |
| CCl₃CH₂ | isopropyl | 3 chloro-4-trifluoromethylphenyl |
| CCl₃CH₂ | isopropyl | 3-chloro-4-trifluromethoxyphenyl |
| CCl₃CH₂ | isopropyl | 3-chloro-4-trifluoromethylthiophenyl |
| CCl₃CH₂ | isopropyl | 2-bromophenyl |
| CCl₃CH₂ | isopropyl | 2-trifluoromethylphenyl |
| CCl₃CH₂ | isopropyl | 3-trifluoromethylphenyl |
| CCl₃CH₂ | isopropyl | 4-trifluoromethylphenyl |
| CCl₃CH₂ | isopropyl | 2-trifluromethoxyphenyl |
| CCl₃CH₂ | isopropyl | 2-difluoromethoxyphenyl |
| CCl₃CH₂ | isopropyl | 2-(2,2,2-trifluoroethoxy)phenyl |
| CCl₃CH₂ | isopropyl | 2-(2,2,2-trifluoroethylthio)phenyl |
| CCl₃CH₂ | isopropyl | 2-trifluoromethylthiophenyl |
| CCl₃CH₂ | isopropyl | 2-methylphenyl |
| CCl₃CH₂ | isopropyl | 3-methylphenyl |
| CCl₃CH₂ | isopropyl | 4-methylphenyl |
| CCl₃CH₂ | isopropyl | 2,3-dimethylphenyl |
| CCl₃CH₂ | isopropyl | 2,4-dimethylphenyl |
| CCl₃CH₂ | isopropyl | 2,6-dimethylphenyl |
| CCl₃CH₂ | isopropyl | 2,4,6-trimethylphenyl |
| CCl₃CH₂ | isopropyl | 2-ethylphenyl |
| CCl₃CH₂ | isopropyl | 3-ethylphenyl |
| CCl₃CH₂ | isopropyl | 4-ethylphenyl |
| CCl₃CH₂ | isopropyl | 2-methoxyphenyl |
| CCl₃CH₂ | isopropyl | 3-methoxyphenyl |
| CCl₃CH₂ | isopropyl | 4-methoxyphenyl |
| CCl₃CH₂ | isopropyl | 2-methylthiophenyl |
| CCl₃CH₂ | isopropyl | 2-nitrophenyl |
| CCl₃CH₂ | isopropyl | 2-cyanophenyl |
| CCl₃CH₂ | isopropyl | 3-chloro-4-trifluoromethylthiophenyl |
| CF₃CH₂ | ethyl | ethyl |
| CF₃CH₂ | ethyl | cyclohexyl |
| CF₃CH₂ | n-propyl | n-propyl |
| CF₃CH₂ | n-propyl | cyclopropyl |
| CF₃CH₂ | n-propyl | cyclopentyl |
| CF₃CH₂ | allyl | allyl |
| CF₃CH₂ | propargyl | propargyl |
| CF₃CH₂ | methyl | phenyl |
| CF₃CH₂ | ethyl | phenyl |
| CF₃CH₂ | n-propyl | phenyl |
| CF₃CH₂ | isopropyl | phenyl |
| CF₃CH₂ | n-butyl | phenyl |
| CF₃CH₂ | s-butyl | phenyl |
| CF₃CH₂ | isobutyl | phenyl |
| CF₃CH₂ | phenyl | phenyl |
| CF₃CH₂ | isopropyl | 2-fluorophenyl |
| CF₃CH₂ | isopropyl | 3-fluorophenyl |
| CF₃CH₂ | isopropyl | 4-fluorophenyl |
| CF₃CH₂ | isopropyl | 2-chlorophenyl |
| CF₃CH₂ | isopropyl | 3-chlorophenyl |
| CF₃CH₂ | isopropyl | 4-chlorophenyl |
| CF₃CH₂ | isopropyl | 2,3-dichlorophenyl |
| CF₃CH₂ | isopropyl | 2,4-dichlorophenyl |
| CF₃CH₂ | isopropyl | 2,5-dichlorophenyl |
| CF₃CH₂ | isopropyl | 2,6-dichlorophenyl |
| CF₃CH₂ | isopropyl | 3,4-dichlorophenyl |
| CF₃CH₂ | isopropyl | 3,5-dichlorophenyl |
| CF₃CH₂ | isopropyl | 2,4,6-trichlorophenyl |
| CF₃CH₂ | isopropyl | 2-chloro-3-methylphenyl |
| CF₃CH₂ | isopropyl | 2-chloro-4-methylphenyl |
| CF₃CH₂ | isopropyl | 2-chloro-5-methylphenyl |
| CF₃CH₂ | isopropyl | 2-chloro-6-methylphenyl |
| CF₃CH₂ | isopropyl | 3-chloro-4-methylphenyl |
| CF₃CH₂ | isopropyl | 3-chloro-4-trifluoromethylphenyl |
| CF₃CH₂ | isopropyl | 3-chloro-4-trifluromethoxyphenyl |
| CF₃CH₂ | isopropyl | 2-bromophenyl |
| CF₃CH₂ | isopropyl | 2-trifluoromethylphenyl |
| CF₃CH₂ | isopropyl | 3-trifluoromethylphenyl |
| CF₃CH₂ | isopropyl | 4-trifluoromethylphenyl |
| CF₃CH₂ | isopropyl | 2-trifluromethoxyphenyl |

TABLE 1-continued

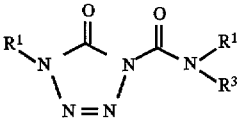

| R¹ | R² | R³ |
|---|---|---|
| CF₃CH₂ | isopropyl | 2-difluoromethoxyphenyl |
| CF₃CH₂ | isopropyl | 2-(2,2,2-trifluoroethoxy)phenyl |
| CF₃CH₂ | isopropyl | 2-(2,2,2-trifluoroethylthio)phenyl |
| CF₃CH₂ | isopropyl | 2-trifluoromethylthiophenyl |
| CF₃CH₂ | isopropyl | 2-methylphenyl |
| CF₃CH₂ | isopropyl | 3-methylphenyl |
| CF₃CH₂ | isopropyl | 4-methylphenyl |
| CF₃CH₂ | isopropyl | 2,3-dimethylphenyl |
| CF₃CH₂ | isopropyl | 2,4-dimethylphenyl |
| CF₃CH₂ | isopropyl | 2,6-dimethylphenyl |
| CF₃CH₂ | isopropyl | 2,4,6-trimethylphenyl |
| CF₃CH₂ | isopropyl | 2-ethylphenyl |
| CF₃CH₂ | isopropyl | 3-ethylphenyl |
| CF₃CH₂ | isopropyl | 4-ethylphenyl |
| CF₃CH₂ | isopropyl | 2-methoxyphenyl |
| CF₃CH₂ | isopropyl | 3-methoxyphenyl |
| CF₃CH₂ | isopropyl | 4-methoxyphenyl |
| CF₃CH₂ | isopropyl | 2-methylthiophenyl |
| CF₃CH₂ | isopropyl | 2-nitrophenyl |
| CF₃CH₂ | isopropyl | 2-cyanophenyl |
| CF₃CF₂ | ethyl | ethyl |
| CF₃CF₂ | ethyl | cyclohexyl |
| CF₃CF₂ | n-propyl | n-propyl |
| CF₃CF₂ | n-propyl | cyclopropyl |
| CF₃CF₂ | n-propyl | cyclopentyl |
| CF₃CF₂ | allyl | allyl |
| CF₃CF₂ | propargyl | propargyl |
| CF₃CF₂ | methyl | phenyl |
| CF₃CF₂ | ethyl | phenyl |
| CF₃CF₂ | n-propyl | phenyl |
| CF₃CF₂ | isopropyl | phenyl |
| CF₃CF₂ | n-butyl | phenyl |
| CF₃CF₂ | s-butyl | phenyl |
| CF₃CF₂ | isobutyl | phenyl |
| CF₃CF₂ | phenyl | phenyl |
| CF₃CF₂ | isopropyl | 2-fluorophenyl |
| CF₃CF₂ | isopropyl | 3-fluorophenyl |
| CF₃CF₂ | isopropyl | 4-fluorophenyl |
| CF₃CF₂ | isopropyl | 2-chlorophenyl |
| CF₃CF₂ | isopropyl | 3-chlorophenyl |
| CF₃CF₂ | isopropyl | 4-chlorophenyl |
| CF₃CF₂ | isopropyl | 2,3-dichlorophenyl |
| CF₃CF₂ | isopropyl | 2,4-dichlorophenyl |
| CF₃CF₂ | isopropyl | 2,5-dichlorophenyl |
| CCl₃CF₂ | isopropyl | 2,6-dichlorophenyl |
| CF₃CF₂ | isopropyl | 3,4-dichlorophenyl |
| CF₃CF₂ | isopropyl | 3,5-dichlorophenyl |
| CF₃CF₂ | isopropyl | 2,4,6-trichlorophenyl |
| CF₃CF₂ | isopropyl | 2-chloro-3-methylphenyl |
| CF₃CF₂ | isopropyl | 2-chloro-4-methylphenyl |
| CF₃CF₂ | isopropyl | 2-chloro-5-methylphenyl |
| CF₃CF₂ | isopropyl | 2-chloro-6-methylphenyl |
| CF₃CF₂ | isopropyl | 3-chloro-4-methylphenyl |
| CF₃CF₂ | isopropyl | 3-chloro-4-trifluoromethylphenyl |
| CF₃CF₂ | isopropyl | 3-chloro-4-trifluromethoxyphenyl |
| CF₃CF₂ | isopropyl | 3-chloro-4-trifluoromethylthiophenyl |
| CF₃CF₂ | isopropyl | 2-bromophenyl |
| CF₃CF₂ | isopropyl | 2-trifluoromethylphenyl |
| CF₃CF₂ | isopropyl | 3-trifluoromethylphenyl |
| CF₃CF₂ | isopropyl | 4-trifluoromethylphenyl |
| CF₃CF₂ | isopropyl | 2-trifluromethoxyphenyl |
| CF₃CF₂ | isopropyl | 2-difluoromethoxyphenyl |
| CF₃CF₂ | isopropyl | 2-(2,2,2-trifluoroethoxy)phenyl |
| CF₃CF₂ | isopropyl | 2-(2,2,2-trifluoroethylthio)phenyl |
| CF₃CF₂ | isopropyl | 2-methylphenyl |
| CF₃CF₂ | isopropyl | 3-methylphenyl |
| CF₃CF₂ | isopropyl | 4-methylphenyl |
| CF₃CF₂ | isopropyl | 2,3-dimethylphenyl |
| CF₃CF₂ | isopropyl | 2,4-dimethylphenyl |
| CF₃CF₂ | isopropyl | 2,6-dimethylphenyl |

TABLE 1-continued

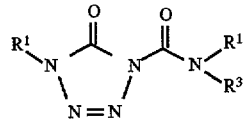

| R¹ | R² | R³ |
|---|---|---|
| CF₃CF₂ | isopropyl | 2,4,6-trimethylphenyl |
| CF₃CF₂ | isopropyl | 2-ethylphenyl |
| CF₃CF₂ | isopropyl | 3-ethylphenyl |
| CF₃CF₂ | isopropyl | 4-ethylphenyl |
| CF₃CF₂ | isopropyl | 2-methoxyphenyl |
| CF₃CF₂ | isopropyl | 3-methoxyphenyl |
| CF₃CF₂ | isopropyl | 4-methoxyphenyl |
| CF₃CF₂ | isopropyl | 2-methylthiophenyl |
| CF₃CF₂ | isopropyl | 2-nitrophenyl |
| CF₃CF₂ | isopropyl | 2-cyanophenyl |
| ClCH₂CH₂CH₂ | ethyl | ethyl |
| ClCH₂CH₂CH₂ | ethyl | cyclohexyl |
| ClCH₂CH₂CH₂ | n-propyl | n-propyl |
| ClCH₂CH₂CH₂ | n-propyl | cyclopropyl |
| ClCH₂CH₂CH₂ | n-propyl | cyclopentyl |
| ClCH₂CH₂CH₂ | allyl | allyl |
| ClCH₂CH₂CH₂ | propargyl | propargyl |
| ClCH₂CH₂CH₂ | methyl | phenyl |
| ClCH₂CH₂CH₂ | ethyl | phenyl |
| ClCH₂CH₂CH₂ | n-propyl | phenyl |
| ClCH₂CH₂CH₂ | isopropyl | phenyl |
| ClCH₂CH₂CH₂ | n-butyl | phenyl |
| ClCH₂CH₂CH₂ | s-butyl | phenyl |
| ClCH₂CH₂CH₂ | isobutyl | phenyl |
| ClCH₂CH₂CH₂ | phenyl | phenyl |
| ClCH₂CH₂CH₂ | isopropyl | 2-fluorophenyl |
| ClCH₂CH₂CH₂ | isopropyl | 3-fluorophenyl |
| ClCH₂CH₂CH₂ | isopropyl | 4-fluorophenyl |
| ClCH₂CH₂CH₂ | isopropyl | 2-chlorophenyl |
| ClCH₂CH₂CH₂ | isopropyl | 3-chlorophenyl |
| ClCH₂CH₂CH₂ | isopropyl | 4-chlorophenyl |
| ClCH₂CH₂CH₂ | isopropyl | 2,3-dichlorophenyl |
| ClCH₂CH₂CH₂ | isopropyl | 2,4-dichlorophenyl |
| ClCH₂CH₂CH₂ | isopropyl | 2,5-dichlorophenyl |
| ClCH₂CH₂CH₂ | isopropyl | 2,6-dichlorophenyl |
| ClCH₂CH₂CH₂ | isopropyl | 3,4-dichlorophenyl |
| ClCH₂CH₂CH₂ | isopropyl | 3,5-dichlorophenyl |
| ClCH₂CH₂CH₂ | isopropyl | 2,4,6-trichlorophenyl |
| ClCH₂CH₂CH₂ | isopropyl | 2-chloro-3-methylphenyl |
| ClCH₂CH₂CH₂ | isopropyl | 2-chloro-4-methylphenyl |
| ClCH₂CH₂CH₂ | isopropyl | 2-chloro-5-methylphenyl |
| ClCH₂CH₂CH₂ | isopropyl | 2-chloro-6-methylphenyl |
| ClCH₂CH₂CH₂ | isopropyl | 3-chloro-4-methylphenyl |
| ClCH₂CH₂CH₂ | isopropyl | 3-chloro-4-trifluoromethylphenyl |
| ClCH₂CH₂CH₂ | isopropyl | 3-chloro-4-trifluromethoxyphenyl |
| ClCH₂CH₂CH₂ | isopropyl | 3-chloro-4-trifluoromethylthiophenyl |
| ClCH₂CH₂CH₂ | isopropyl | 2-bromophenyl |
| ClCH₂CH₂CH₂ | isopropyl | 2-trifluoromethylphenyl |
| ClCH₂CH₂CH₂ | isopropyl | 3-trifluoromethylphenyl |
| ClCH₂CH₂CH₂ | isopropyl | 4-trifluoromethylphenyl |
| ClCH₂CH₂CH₂ | isopropyl | 2-trifluromethoxyphenyl |
| ClCH₂CH₂CH₂ | isopropyl | 2-difluoromethoxyphenyl |
| ClCH₂CH₂CH₂ | isopropyl | 2-(2,2,2-trifluoroethoxy)phenyl |
| ClCH₂CH₂CH₂ | isopropyl | 2-(2,2,2-trifluoroethylthio)phenyl |
| ClCH₂CH₂CH₂ | isopropyl | 2-methylphenyl |
| ClCH₂CH₂CH₂ | isopropyl | 3-methylphenyl |
| ClCH₂CH₂CH₂ | isopropyl | 4-methylphenyl |
| ClCH₂CH₂CH₂ | isopropyl | 2,3-dimethylphenyl |
| ClCH₂CH₂CH₂ | isopropyl | 2,4-dimethylphenyl |
| ClCH₂CH₂CH₂ | isopropyl | 2,6-dimethylphenyl |
| ClCH₂CH₂CH₂ | isopropyl | 2,4,6-trimethylphenyl |
| ClCH₂CH₂CH₂ | isopropyl | 2-ethylphenyl |
| ClCH₂CH₂CH₂ | isopropyl | 3-ethylphenyl |
| ClCH₂CH₂CH₂ | isopropyl | 4-ethylphenyl |
| ClCH₂CH₂CH₂ | isopropyl | 2-methoxyphenyl |
| ClCH₂CH₂CH₂ | isopropyl | 3-methoxyphenyl |
| ClCH₂CH₂CH₂ | isopropyl | 4-methoxyphenyl |
| ClCH₂CH₂CH₂ | isopropyl | 2-methylthiophenyl |
| ClCH₂CH₂CH₂ | isopropyl | 2-nitrophenyl |
| ClCH₂CH₂CH₂ | isopropyl | 2-cyanophenyl |

TABLE 1-continued

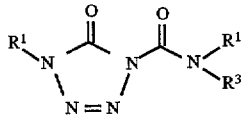

| R¹ | R² | R³ |
|---|---|---|
| FCH₂CH₂CH₂ | ethyl | ethyl |
| FCH₂CH₂CH₂ | ethyl | cyclohexyl |
| FCH₂CH₂CH₂ | n-propyl | n-propyl |
| FCH₂CH₂CH₂ | n-propyl | cyclopropyl |
| FCH₂CH₂CH₂ | n-propyl | cyclopentyl |
| FCH₂CH₂CH₂ | allyl | allyl |
| FCH₂CH₂CH₂ | propargyl | propargyl |
| FCH₂CH₂CH₂ | methyl | phenyl |
| FCH₂CH₂CH₂ | ethyl | phenyl |
| FCH₂CH₂CH₂ | n-propyl | phenyl |
| FCH₂CH₂CH₂ | isopropyl | phenyl |
| FCH₂CH₂CH₂ | n-butyl | phenyl |
| FCH₂CH₂CH₂ | s-butyl | phenyl |
| FCH₂CH₂CH₂ | isobutyl | phenyl |
| FCH₂CH₂CH₂ | phenyl | phenyl |
| FCH₂CH₂CH₂ | isopropyl | 2-fluorophenyl |
| FCH₂CH₂CH₂ | isopropyl | 3-fluorophenyl |
| FCH₂CH₂CH₂ | isopropyl | 4-fluorophenyl |
| FCH₂CH₂CH₂ | isopropyl | 2-chlorophenyl |
| FCH₂CH₂CH₂ | isopropyl | 3-chlorophenyl |
| FCH₂CH₂CH₂ | isopropyl | 4-chlorophenyl |
| FCH₂CH₂CH₂ | isopropyl | 2,3-dichlorophenyl |
| FCH₂CH₂CH₂ | isopropyl | 2,4-dichlorophenyl |
| FCH₂CH₂CH₂ | isopropyl | 2,5-dichlorophenyl |
| FCH₂CH₂CH₂ | isopropyl | 2,6-dichlorophenyl |
| FCH₂CH₂CH₂ | isopropyl | 3,4-dichlorophenyl |
| FCH₂CH₂CH₂ | isopropyl | 3,5-dichlorophenyl |
| FCH₂CH₂CH₂ | isopropyl | 2,4,6-trichlorophenyl |
| FCH₂CH₂CH₂ | isopropyl | 2-chloro-3-methylphenyl |
| FCH₂CH₂CH₂ | isopropyl | 2-chloro-4-methylphenyl |
| FCH₂CH₂CH₂ | isopropyl | 2-chloro-5-methylphenyl |
| FCH₂CH₂CH₂ | isopropyl | 2-chloro-6-methylphenyl |
| FCH₂CH₂CH₂ | isopropyl | 3-chloro-4-methylphenyl |
| FCH₂CH₂CH₂ | isopropyl | 3-chloro-4-trifluoromethylphenyl |
| FCH₂CH₂CH₂ | isopropyl | 3-chloro-4-trifluromethoxyphenyl |
| FCH₂CH₂CH₂ | isopropyl | 3-chloro-4-trifluoromethylthiophenyl |
| FCH₂CH₂CH₂ | isopropyl | 2-bromophenyl |
| FCH₂CH₂CH₂ | isopropyl | 2-trifluoromethylphenyl |
| FCH₂CH₂CH₂ | isopropyl | 3-trifluoromethylphenyl |
| FCH₂CH₂CH₂ | isopropyl | 4-trifluoromethylphenyl |
| FCH₂CH₂CH₂ | isopropyl | 2-trifluromethoxyphenyl |
| FCH₂CH₂CH₂ | isopropyl | 2-difluoromethoxyphenyl |
| FCH₂CH₂CH₂ | isopropyl | 2-(2,2,2-trifluoroethoxy)phenyl |
| FCH₂CH₂CH₂ | isopropyl | 2-(2,2,2-trifluoroethylthio)phenyl |
| FCH₂CH₂CH₂ | isopropyl | 2-methylphenyl |
| FCH₂CH₂CH₂ | isopropyl | 3-methylphenyl |
| FCH₂CH₂CH₂ | isopropyl | 4-methylphenyl |
| FCH₂CH₂CH₂ | isopropyl | 2,3-dimethylphenyl |
| FCH₂CH₂CH₂ | isopropyl | 2,4-dimethylphenyl |
| FCH₂CH₂CH₂ | isopropyl | 2,6-dimethylphenyl |
| FCH₂CH₂CH₂ | isopropyl | 2,4,6-trimethylphenyl |
| FCH₂CH₂CH₂ | isopropyl | 2-ethylphenyl |
| FCH₂CH₂CH₂ | isopropyl | 3-ethylphenyl |
| FCH₂CH₂CH₂ | isopropyl | 4-ethylphenyl |
| FCH₂CH₂CH₂ | isopropyl | 2-methoxyphenyl |
| FCH₂CH₂CH₂ | isopropyl | 3-methoxyphenyl |
| FCH₂CH₂CH₂ | isopropyl | 4-methoxyphenyl |
| FCH₂CH₂CH₂ | isopropyl | 2-methylthiophenyl |
| FCH₂CH₂CH₂ | isopropyl | 2-nitrophenyl |
| FCH₂CH₂CH₂ | isopropyl | 2-cyanophenyl |
| CF₃CF₂CH₂ | ethyl | ethyl |
| CF₃CF₂CH₂ | ethyl | cyclohexyl |
| CF₃CF₂CH₂ | n-propyl | n-propyl |
| CF₃CF₂CH₂ | n-propyl | cyclopropyl |
| CF₃CF₂CH₂ | n-propyl | cyclopentyl |
| CF₃CF₂CH₂ | allyl | allyl |
| CF₃CF₂CH₂ | propargyl | propargyl |
| CF₃CF₂CH₂ | methyl | phenyl |
| CF₃CF₂CH₂ | ethyl | phenyl |
| CF₃CF₂CH₂ | n-propyl | phenyl |

TABLE 1-continued

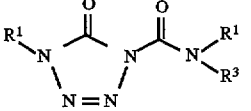

| R¹ | R² | R³ |
|---|---|---|
| CF₃CF₂CH₂ | isopropyl | phenyl |
| CF₃CF₂CH₂ | n-butyl | phenyl |
| CF₃CF₂CH₂ | s-butyl | phenyl |
| CF₃CF₂CH₂ | isobutyl | phenyl |
| CF₃CF₂CH₂ | phenyl | phenyl |
| CF₃CF₂CH₂ | isopropyl | 2-fluorophenyl |
| CF₃CF₂CH₂ | isopropyl | 3-fluorophenyl |
| CF₃CF₂CH₂ | isopropyl | 4-fluorophenyl |
| CF₃CF₂CH₂ | isopropyl | 2-chlorophenyl |
| CF₃CF₂CH₂ | isopropyl | 3-chlorophenyl |
| CF₃CF₂CH₂ | isopropyl | 4-chlorophenyl |
| CF₃CF₂CH₂ | isopropyl | 2,3-dichlorophenyl |
| CF₃CF₂CH₂ | isopropyl | 2,4-dichlorophenyl |
| CF₃CF₂CH₂ | isopropyl | 2,5-dichlorophenyl |
| CF₃CF₂CH₂ | isopropyl | 2,6-dichlorophenyl |
| CF₃CF₂CH₂ | isopropyl | 3,4-dichlorophenyl |
| CF₃CF₂CH₂ | isopropyl | 3,5-dichlorophenyl |
| CF₃CF₂CH₂ | isopropyl | 2,4,6-trichlorophenyl |
| CF₃CF₂CH₂ | isopropyl | 2-chloro-3-methylphenyl |
| CF₃CF₂CH₂ | isopropyl | 2-chloro-4-methylphenyl |
| CF₃CF₂CH₂ | isopropyl | 2-chloro-5-methylphenyl |
| CF₃CF₂CH₂ | isopropyl | 2-chloro-6-methylphenyl |
| CF₃CF₂CH₂ | isopropyl | 3-chloro-4-methylphenyl |
| CF₃CF₂CH₂ | isopropyl | 3-chloro-4-trifluoromethylphenyl |
| CF₃CF₂CH₂ | isopropyl | 3-chloro-4-trifluromethoxyphenyl |
| CF₃CF₂CH₂ | isopropyl | 3-chloro-4-trifluoromethylthiophenyl |
| CF₃CF₂CH₂ | isopropyl | 2-bromophenyl |
| CF₃CF₂CH₂ | isopropyl | 2-trifluoromethylphenyl |
| CF₃CF₂CH₂ | isopropyl | 3-trifluoromethylphenyl |
| CF₃CF₂CH₂ | isopropyl | 4-trifluoromethylphenyl |
| CF₃CF₂CH₂ | isopropyl | 2-trifluromethoxyphenyl |
| CF₃CF₂CH₂ | isopropyl | 2-difluoromethoxyphenyl |
| CF₃CF₂CH₂ | isopropyl | 2-(2,2,2-trifluoroethoxy)phenyl |
| CF₃CF₂CH₂ | isopropyl | 2-(2,2,2-trifluoroethylthio)phenyl |
| CF₃CF₂CH₂ | isopropyl | 2-methylphenyl |
| CF₃CF₂CH₂ | isopropyl | 3-methylphenyl |
| CF₃CF₂CH₂ | isopropyl | 4-methylphenyl |
| CF₃CF₂CH₂ | isopropyl | 2,3-dimethylphenyl |
| CF₃CF₂CH₂ | isopropyl | 2,4-dimethylphenyl |
| CF₃CF₂CH₂ | isopropyl | 2,6-dimethylphenyl |
| CF₃CF₂CH₂ | isopropyl | 2,4,6-trimethylphenyl |
| CF₃CF₂CH₂ | isopropyl | 2-ethylphenyl |
| CF₃CF₂CH₂ | isopropyl | 3-ethylphenyl |
| CF₃CF₂CH₂ | isopropyl | 4-ethylphenyl |
| CF₃CF₂CH₂ | isopropyl | 2-methoxyphenyl |
| CF₃CF₂CH₂ | isopropyl | 3-methoxyphenyl |
| CF₃CF₂CH₂ | isopropyl | 4-methoxyphenyl |
| CF₃CF₂CH₂ | isopropyl | 2-methylthiophenyl |
| CF₃CF₂CH₂ | isopropyl | 2-nitrophenyl |
| CF₃CF₂CH₂ | isopropyl | 2-cyanophenyl |
| CF₃CF₂CF₂ | ethyl | ethyl |
| CF₃CF₂CF₂ | ethyl | cyclohexyl |
| CF₃CF₂CF₂ | n-propyl | n-propyl |
| CF₃CF₂CF₂ | n-propyl | cyclopropyl |
| CF₃CF₂CF₂ | n-propyl | cyclopentyl |
| CF₃CF₂CF₂ | allyl | allyl |
| CF₃CF₂CF₂ | propargyl | propargyl |
| CF₃CF₂CF₂ | methyl | phenyl |
| CF₃CF₂CF₂ | ethyl | phenyl |
| CF₃CF₂CF₂ | n-propyl | phenyl |
| CF₃CF₂CF₂ | isopropyl | phenyl |
| CF₃CF₂CF₂ | n-butyl | phenyl |
| CF₃CF₂CF₂ | s-butyl | phenyl |
| CF₃CF₂CF₂ | isobutyl | phenyl |
| CF₃CF₂CF₂ | phenyl | phenyl |
| CF₃CF₂CF₂ | isopropyl | 2-fluorophenyl |
| CF₃CF₂CF₂ | isopropyl | 3-fluorophenyl |
| CF₃CF₂CF₂ | isopropyl | 4-fluorophenyl |
| CF₃CF₂CF₂ | isopropyl | 2-chlorophenyl |
| CF₃CF₂CF₂ | isopropyl | 3-chlorophenyl |

TABLE 1-continued

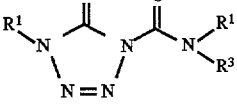

| R¹ | R² | R³ |
|---|---|---|
| $CF_3CF_2CF_2$ | isopropyl | 4-chlorophenyl |
| $CF_3CF_2CF_2$ | isopropyl | 2,3-dichlorophenyl |
| $CF_3CF_2CF_2$ | isopropyl | 2,4-dichlorophenyl |
| $CF_3CF_2CF_2$ | isopropyl | 2,5-dichlorophenyl |
| $CF_3CF_2CF_2$ | isopropyl | 2,6-dichlorophenyl |
| $CF_3CF_2CF_2$ | isopropyl | 3,4-dichlorophenyl |
| $CF_3CF_2CF_2$ | isopropyl | 3,5-dichlorophenyl |
| $CF_3CF_2CF_2$ | isopropyl | 2,4,6-trichlorophenyl |
| $CF_3CF_2CF_2$ | isopropyl | 2-chloro-3-methylphenyl |
| $CF_3CF_2CF_2$ | isopropyl | 2-chloro-4-methylphenyl |
| $CF_3CF_2CF_2$ | isopropyl | 2-chloro-5-methylphenyl |
| $CF_3CF_2CF_2$ | isopropyl | 2-chloro-6-methylphenyl |
| $CF_3CF_2CF_2$ | isopropyl | 3-chloro-4-methylphenyl |
| $CF_3CF_2CF_2$ | isopropyl | 3-chloro-4-trifluoromethylphenyl |
| $CF_3CF_2CF_2$ | isopropyl | 3-chloro-4-trifluromethoxyphenyl |
| $CF_3CF_2CF_2$ | isopropyl | 3-chloro-4-trifluoromethylthiophenyl |
| $CF_3CF_2CF_2$ | isopropyl | 2-bromophenyl |
| $CF_3CF_2CF_2$ | isopropyl | 2-trifluoromethylphenyl |
| $CF_3CF_2CF_2$ | isopropyl | 3-trifluoromethylphenyl |
| $CF_3CF_2CF_2$ | isopropyl | 4-trifluoromethylphenyl |
| $CF_3CF_2CF_2$ | isopropyl | 2-trifluromethoxyphenyl |
| $CF_3CF_2CF_2$ | isopropyl | 2-difluoromethoxyphenyl |
| $CF_3CF_2CF_2$ | isopropyl | 2-(2,2,2-trifluoroethoxy)phenyl |
| $CF_3CF_2CF_2$ | isopropyl | 2-(2,2,2-trifluoroethylthio)phenyl |
| $CF_3CF_2CF_2$ | isopropyl | 2-methylphenyl |
| $CF_3CF_2CF_2$ | isopropyl | 3-methylphenyl |
| $CF_3CF_2CF_2$ | isopropyl | 4-methylphenyl |
| $CF_3CF_2CF_2$ | isopropyl | 2,3-dimethylphenyl |
| $CF_3CF_2CF_2$ | isopropyl | 2,4-dimethylphenyl |
| $CF_3CF_2CF_2$ | isopropyl | 2,6-dimethylphenyl |
| $CF_3CF_2CF_2$ | isopropyl | 2,4,6-trimethylphenyl |
| $CF_3CF_2CF_2$ | isopropyl | 2-ethylphenyl |
| $CF_3CF_2CF_2$ | isopropyl | 3-ethylphenyl |
| $CF_3CF_2CF_2$ | isopropyl | 4-ethylphenyl |
| $CF_3CF_2CF_2$ | isopropyl | 2-methoxyphenyl |
| $CF_3CF_2CF_2$ | isopropyl | 3-methoxyphenyl |
| $CF_3CF_2CF_2$ | isopropyl | 4-methoxyphenyl |
| $CF_3CF_2CF_2$ | isopropyl | 2-methylthiophenyl |
| $CF_3CF_2CF_2$ | isopropyl | 2-nitrophenyl |
| $CF_3CF_2CF_2$ | isopropyl | 2-cyanophenyl |

TABLE 2

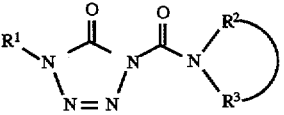

| R¹ | $-N\begin{matrix}R^2\\R^3\end{matrix}$ |
|---|---|
| $ClCH_2$ | piperidino |
| $ClCH_2$ | 2-methylpiperidino |
| $ClCH_2$ | indol-1-yl |
| $ClCH_2$ | perhydroindol-1-yl |
| $ClCH_2$ | 1,2,3,4-tetrahydroquinolin-1-yl |
| $ClCH_2$ | 2-methyl-1,2,3,4-tetrahydroquinolin-1-yl |
| $BrCH_2$ | piperidino |
| $BrCH_2$ | 2-methylpiperidino |
| $BrCH_2$ | indol-1-yl |
| $BrCH_2$ | perhydroindol-1-yl |
| $BrCH_2$ | 1,2,3,4-tetrahydroquinolin-1-yl |
| $BrCH_2$ | 2-methyl-1,2,3,4-tetrahydroquinolin-1-yl |

TABLE 2-continued

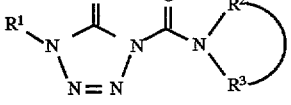

| R¹ | $-N\begin{matrix}R^2\\R^3\end{matrix}$ |
|---|---|
| $FCH_2$ | piperidino |
| $FCH_2$ | 2-methylpiperidino |
| $FCH_2$ | indol-1-yl |
| $FCH_2$ | perhydroindol-1-yl |
| $FCH_2$ | 1,2,3,4-tetrahydroquinolin-1-yl |
| $FCH_2$ | 2-methyl-1,2,3,4-tetrahydroquinolin-1-yl |
| $Cl_2HC$ | piperidino |
| $Cl_2HC$ | 2-methylpiperidino |
| $Cl_2HC$ | indol-1-yl |
| $Cl_2HC$ | perhydroindol-1-yl |
| $Cl_2HC$ | 1,2,3,4-tetrahydroquinolin-1-yl |
| $Cl_2HC$ | 2-methyl-1,2,3,4-tetrahydroquinolin-1-yl |
| $F_2HC$ | piperidino |
| $F_2HC$ | 2-methylpiperidino |
| $F_2HC$ | indol-1-yl |
| $F_2HC$ | perhydroindol-1-yl |
| $F_2HC$ | 1,2,3,4-tetrahydroquinolin-1-yl |
| $F_2HC$ | 2-methyl-1,2,3,4-tetrahydroquinolin-1-yl |
| $Cl_3C$ | piperidino |
| $Cl_3C$ | 2-methylpiperidino |
| $Cl_3C$ | indol-1-yl |
| $Cl_3C$ | perhydroindol-1-yl |
| $Cl_3C$ | 1,2,3,4-tetrahydroquinolin-1-yl |
| $Cl_3C$ | 2-methyl-1,2,3,4-tetrahydroquinolin-1-yl |
| $F_3C$ | piperidino |
| $F_3C$ | 2-methylpiperidino |
| $F_3C$ | indol-1-yl |
| $F_3C$ | perhydroindol-1-yl |
| $F_3C$ | 1,2,3,4-tetrahydroquinolin-1-yl |
| $F_3C$ | 2-methyl-1,2,3,4-tetrahydroquinolin-1-yl |
| $F_2ClC$ | piperidino |
| $F_2ClC$ | 2-methylpiperidino |
| $F_2ClC$ | indol-1-yl |
| $F_2ClC$ | perhydroindol-1-yl |
| $F_2ClC$ | 1,2,3,4-tetrahydroquinolin-1-yl |
| $F_2ClC$ | 2-methyl-1,2,3,4-tetrahydroquinolin-1-yl |
| $CH_3CHCl$ | piperidino |
| $CH_3CHCl$ | 2-methylpiperidino |
| $CH_3CHCl$ | indol-1-yl |
| $CH_3CHCl$ | perhydroindol-1-yl |
| $CH_3CHCl$ | 1,2,3,4-tetrahydroquinolin-1-yl |
| $CH_3CHCl$ | 2-methyl-1,2,3,4-tetrahydroquinolin-1-yl |
| $CH_3CHBr$ | piperidino |
| $CH_3CHBr$ | 2-methylpiperidino |
| $CH_3CHBr$ | indol-1-yl |
| $CH_3CHBr$ | perhydroindol-1-yl |
| $CH_3CHBr$ | 1,2,3,4-tetrahydroquinolin-1-yl |
| $CH_3CHBr$ | 2-methyl-1,2,3,4-tetrahydroquinolin-1-yl |
| $CH_3CHF$ | piperidino |
| $CH_3CHF$ | 2-methylpiperidino |
| $CH_3CHF$ | indol-1-yl |
| $CH_3CHF$ | perhydroindol-1-yl |
| $CH_3CHF$ | 1,2,3,4-tetrahydroquinolin-1-yl |
| $CH_3CHF$ | 2-methyl-1,2,3,4-tetrahydroquinolin-1-yl |
| $ClCH_2CH_2$ | piperidino |
| $ClCH_2CH_2$ | 2-methylpiperidino |
| $ClCH_2CH_2$ | indol-1-yl |
| $ClCH_2CH_2$ | 1,2,3,4-tetrahydroquinolin-1-yl |
| $ClCH_2CH_2$ | 2-methyl-1,2,3,4-tetrahydroquinolin-1-yl |
| $BrCH_2CH_2$ | piperidino |
| $BrCH_2CH_2$ | 2-methylpiperidino |
| $BrCH_2CH_2$ | indolin-1-yl |
| $BrCH_2CH_2$ | 1,2,3,4-tetrahydroquinolin-1-yl |
| $BrCH_2CH_2$ | 2-methyl-1,2,3,4-tetrahydroquinolin-1-yl |
| $FCH_2CH_2$ | piperidino |
| $FCH_2CH_2$ | 2-methylpiperidino |

TABLE 2-continued $$R^1-N-\overset{O}{\underset{N=N}{C}}-N-\overset{O}{C}-N\overset{R^2}{\underset{R^3}{\diagup}}$$

$$-N\overset{R^2}{\underset{R^3}{\diagup}}$$

| R¹ | |
|---|---|
| FCH₂CH₂ | indol-1-yl |
| FCH₂CH₂ | 1,2,3,4-tetrahydroquinolin-1-yl |
| FCH₂CH₂ | 2-methyl-1,2,3,4-tetrahydroquinolin-1-yl |
| CH₃CCl₂ | piperidino |
| CH₃CCl₂ | 2-methylpiperidino |
| CH₃CCl₂ | indolin-1-yl |
| CH₃CCl₂ | perhydroindol-1-yl |
| CH₃CCl₂ | 1,2,3,4-tetrahydroquinolin-1-yl |
| CH₃CCl₂ | 2-methyl-1,2,3,4-tetrahydroquinolin-1-yl |
| ClCH₂CHCl | piperidino |
| ClCH₂CHCl | 2-methylpiperidino |
| ClCH₂CHCl | indol-1-yl |
| ClCH₂CHCl | perhydroindol-1-yl |
| ClCH₂CHCl | 1,2,3,4-tetrahydroquinolin-1-yl |
| ClCH₂CHCl | 2-methyl-1,2,3,4-tetrahydroquinolin-1-yl |
| BrCH₂CHBr | piperidino |
| BrCH₂CHBr | 2-methylpiperidino |
| BrCH₂CHBr | indol-1-yl |
| BrCH₂CHBr | perhydroindol-1-yl |
| BrCH₂CHBr | 1,2,3,4-tetrahydroquinolin-1-yl |
| BrCH₂CHBr | 2-methyl-1,2,3,4-tetrahydroquinolin-1-yl |
| FCH₂CHF | piperidino |
| FCH₂CHF | 2-methylpiperidino |
| FCH₂CHF | indol-1-yl |
| FCH₂CHF | perhydroindol-1-yl |
| FCH₂CHF | 1,2,3,4-tetrahydroquinolin-1-yl |
| FCH₂CHF | 2-methyl-1,2,3,4-tetrahydroquinolin-1-yl |
| CCl₃CH₂ | piperidino |
| CCl₃CH₂ | 2-methylpiperidino |
| CCl₃CH₂ | indol-1-yl |
| CCl₃CH₂ | perhydroindol-1-yl |
| CCl₃CH₂ | 1,2,3,4-tetrahydroquinolin-1-yl |
| CCl₃CH₂ | 2-methyl-1,2,3,4-tetrahydroquinolin-1-yl |
| CF₃CH₂ | piperidino |
| CF₃CH₂ | 2-methylpiperidino |
| CF₃CH₂ | indolin-1-yl |
| CF₃CH₂ | perhydroindol-1-yl |
| CF₃CH₂ | 1,2,3,4-tetrahydroquinolin-1-yl |
| CF₃CH₂ | 2-methyl-1,2,3,4-tetrahydroquinolin-1-yl |
| CF₃CF₂ | piperidino |
| CF₃CF₂ | 2-methylpiperidino |
| CF₃CF₂ | indol-1-yl |
| CF₃CF₂ | perhydroindol-1-yl |
| CF₃CF₂ | 1,2,3,4-tetrahydroquinolin-1-yl |
| CF₃CF₂ | 2-methyl-1,2,3,4-tetrahydroquinolin-1-yl |
| ClCH₂CH₂CH₂ | piperidino |
| ClCH₂CH₂CH₂ | 2-methylpiperidino |
| ClCH₂CH₂CH₂ | indol-1-yl |
| ClCH₂CH₂CH₂ | perhydroindol-1-yl |
| ClCH₂CH₂CH₂ | 1,2,3,4-tetrahydroquinolin-1-yl |
| ClCH₂CH₂CH₂ | 2-methyl-1,2,3,4-tetrahydroquinolin-1-yl |
| FCH₂CH₂CH₂ | piperidino |
| FCH₂CH₂CH₂ | 2-methylpiperidino |
| FCH₂CH₂CH₂ | indol-1-yl |
| FCH₂CH₂CH₂ | perhydroindol-1-yl |
| FCH₂CH₂CH₂ | 1,2,3,4-tetrahydroquinolin-1-yl |
| FCH₂CH₂CH₂ | 2-methyl-1,2,3,4-tetrahydroquinolin-1-yl |
| CF₃CF₂CH₂ | piperidino |
| CF₃CF₂CH₂ | 2-methylpiperidino |
| CF₃CF₂CH₂ | indol-1-yl |
| CF₃CF₂CH₂ | perhydroindol-1-yl |
| CF₃CF₂CH₂ | 1,2,3,4-tetrahydroquinolin-1-yl |
| CF₃CF₂CH₂ | 2-methyl-1,2,3,4-tetrahydroquinolin-1-yl |
| CF₃CF₂CF₂ | piperidino |
| CF₃CF₂CF₂ | 2-methylpiperidino |
| CF₃CF₂CF₂ | indol-1-yl |
| CF₃CF₂CF₂ | perhydroindol-1-yl |
| CF₃CF₂CF₂ | 1,2,3,4-tetrahydroquinolin-1-yl |
| CF₃CF₂CF₂ | 2-methyl-1,2,3,4-tetrahydroquinolin-1-yl |

If, for example, 1-(2-chloroethyl)-5(4H)-tetrazolinone and N-isopropyl-N-phenyl carbamoyl chloride are used as the starting materials, the reaction is illustrated by the following equation:

$$Cl-CH_2-CH_2\underset{N=N}{\overset{O}{\underset{N}{\diagdown}}}\overset{H}{\underset{}{N}} +$$

$$\underset{}{\overset{O}{Cl-C-N}}\overset{CH_3}{\underset{}{\overset{|}{CH-CH_3}}}\text{(phenyl)} \xrightarrow[-HCl]{\text{Base}}$$

$$Cl-CH_2-CH_2\underset{N=N}{\overset{O}{\underset{N}{\diagdown}}}\overset{O}{\underset{}{C}}-N\overset{CH_3}{\underset{}{\overset{|}{CH-CH_3}}}\text{(phenyl)}$$

In process (a) according to the invention, starting compounds of the formula (II) mean compounds based on the above definition of R¹, preferably compounds based on the above preferred definitions.

The starting compounds of the formula (II) are novel, and can be obtained by the following processes:

(b) compounds of the formula:

$$R^1-NCO \qquad (IV)$$

wherein R¹ is defined as above, are reacted with trimethylsilyl azide, if appropriate in the presence of catalysts, and then are reacted with portic solvents, or, (c) compounds represented by the above formula (IV) are reacted with sodium azide, in the presence of catalysts and in the presence of inert solvents, or, (d) compounds represented by the formula:

   (V)

wherein R¹ is defined as above,
are reacted with trimethylsilyl azide, and then are reacted with portic solvents, or, (e) compounds represented by the formula:

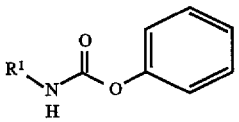   (VI)

wherein R¹ is as defined above,
are reacted with sodium azide, in the presence of catalysts and in the presence of inert solvents, or, (f) compounds represented by the formula:

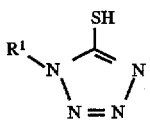   (VII)

wherein R¹ is as defined above,
are reacted with compounds represented by the formula:

   (VIII)

wherein R⁴ is hydrogen, methyl or ethyl,
in the presence of acid binders, if appropriate in the presence of inert solvents.

In the processes (b) and (c), the compounds of formula (IV) used as starting material are known per se and specific examples thereof include the following compounds:
2-chloroethyl isocyanate, 2-bromoethyl isocyanate, 2-fluoroethyl isocyanate, 1-chloroethyl isocyanate, 1-bromoethyl isocyanate, 1,2-dichloroethyl isocyanate, 1,2-dibromoethyl isocyanate, chloromethyl isocyanate, bromomethyl isocyanate, dichloromethyl isocyanate, trichloromethyl isocyanate, trifluoromethyl isocyanate, 3-chloropropyl isocyanate, 3-bromopropyl isocyanate, 3-fluoropropyl isocyanate, 2,2,3,3,3-pentafluoropropyl isocyanate, perfluoropropyl isocyanate, and the like.

In the process (d), the compounds of formula (V) used as starting material are known per se and specific examples thereof include the following compounds:
2-chloropropionyl chloride, 2-bromopropionyl chloride, 3-chloropropionyl chloride, 3-bromopropionyl chloride, 2,3-dichloropropionyl chloride, 2,3-dibromopropionyl chloride, perfluoropropionyl chloride, 3-chlorotetrafluoropropionyl chloride, 1,1,2,2-tetrafluoropropionyl chloride, chloroacetyl chloride, bromoacetyl chloride, dichloroacetyl chloride, trichloroacetyl chloride, trifluoroacetyl chloride, 4-chlorobutyryl chloride, 3,4-dichloropentafluorobutyryl chloride, and the like.

The compounds of above formula (V) can be easily obtained by chlorinating of the formula:

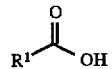   (IX)

wherein R¹ is as defined above, according to conventional method.

Compounds of formula (IX) are known per se and include the following:
2-chloropropionic acid, 2-bromopropionic acid, 3-chloropropionic acid, 3-bromopropionic acid, 2,3-dichloropropionic acid, 2,3-dibromopropionic acid, perfluoropropionic acid, 3-chloro-tetrafluoropropionic acid, 1,1,2,2-tetrafluoropropionic acid, chloroacetic acid, bromoacetic acid, dichloroacetic acid, trichloroacetic acid, trifluoroacetic acid, 4-chlorobutyric acid, 3,4-di-chloropentafluoro butyric acid, and the like.

In the above process (e), compounds of formula (VI) are known and include following:
phenyl-N-(2-chloroethyl) carbamate, phenyl-N-(2-bromoethyl) carbamate, phenyl-N-(2-fluoroethyl) carbamate, phenyl-N-(2,2,2-trifluoroethyl) carbamate, phenyl-N-(2,2,3,3,3-pentafluoro-propyl) carbamate, phenyl-N-(3-chloropropyl) carbamate, and the like.

In the process (f), compounds of formula (VII) used as starting material are novel, and can be obtained compounds of the following formula:

   (X)

wherein
R¹ is defined as above, and R⁵ is $C_{1-4}$ alkyl, are reacted with sodium azide, in the presence of inert solvents.

This reaction can be conducted, for example, by the method known per se and described in Berichte, Vol. 28, pp. 74–76, 1895.

The compounds (X) used in the above process (f) are known per se and are specifically exemplified by the following compounds:
methyl (or ethyl) {N-(2,2,2-trifluoroethyl)}dithio carbamate, methyl (or ethyl) {N-(2-chloroethyl)}dithio carbamate, methyl (or ethyl) {N-(2-bromoethyl)}dithio carbamate, methyl (or ethyl) {N-(2-fluoroethyl)} dithio carbamate, methyl (or ethyl) {N-(2,2,3,3,3-pentafluoropropyl)} dithio carbamate, methyl (or ethyl) {N-(3-chloropropyl) }dithio carbamate, and the like.

In the process (a) according to the invention, starting compounds of the formula (III) mean compounds based on the above definition of R², R³ and hal, preferably compounds based on the above preferred definitions.

In the process (a), compounds of formula (III) used as starting material are known per se and exemplified by the following compounds:
diisopropylcarbamoyl chloride (and bromide), diethylcarbamoyl chloride (and bromide), dimethylcarbamoyl chloride (and bromide), dipropargylcarbamoyl chloride (and bromide), diallylcarbamoyl chloride (and bromide), N-methyl-N-ethylcarbamoyl chloride (and bromide), N-methyl-N-n-propylcarbamoyl chloride (and bromide), N-methyl-N-isopropylcarbamoyl chloride (and bromide), N-methyl-N-cyclopropylcarbamoyl chloride (or bromide), N-methyl-N-sec-butylcarbamoyl chloride (and bromide), N-methyl-N-cyclopentylcarbamoyl chloride (and bromide), N-methyl-N-cyclohexylcarbamoyl chloride (and bromide), N-methyl-N-phenylcarbamoyl chloride (and bromide), N-methyl-N-1-methyl-2-propenylcarbamoyl chloride (and bromide), N-ethyl-N-n-propylcarbamoyl chloride (and bromide), N-ethyl-N-cyclopropylcarbamoyl chloride (and bromide), N-ethyl N-cyclopropylcarbamoyl chloride (and bromide), N-ethyl-N-sec-butylcarbamoyl chloride (and bromide), N-ethyl-N-cyclopentylcarbamoyl chloride (and bromide), N-ethyl-N-cyclohexylcarbamoyl chloride (and bromide), N-ethyl-N-phenylcarbamoyl chloride (and bromide), N-n-propyl-N-iso-propylcarbamoyl chloride (and bromide), N-n-propyl-N-cyclopropylcarbamoyl chloride (and bromide), N-n-propyl-N-sec-butylcarbamoyl chloride (and bromide), N-n-propyl-N-cyclopentylcarbamoyl chloride (and bromide), N-n-propyl-N-cyclohexylcarbamoyl chloride (and bromide), N-isopropyl-N-phenylcarbamoyl chloride (and bromide), N-isopropyl-N-allylcarbamoyl chloride (and bromide), 1-pyrrolidine-carbonyl chloride (and bromide), 1-piperidinecarbonyl chloride (and bromide), 4-morpholinecarbonyl chloride (and bromide), 1-(2-methyl-piperidine)carbonyl chloride (and bromide), 1-(2,5-di-methylpyrrolidine)carbonyl chloride (and bromide), 1-(2,6-dimethylpiperidine)carbonyl chloride (and bromide), 1-(2-methyl-1,2,3,4-tetrahydroquinoline)-carbonyl chloride (and bromide), 1-(perhydroindole)-carbonyl chloride (and bromide), and 1-(perhydroquinoline)-carbonyl chloride (and bromide).

As appropriate diluents for carrying out the process (a) according to the invention there may be mentioned any kind of inert solvents.

Examples of such diluents are aliphatic, alicyclic and aromatic hydrocarbons (which may optionally be chlorinated) such as pentane, hexane, cyclohexane, petroleum ether, ligroin, benzene, toluene, xylene, di-chloromethane, chloroform, carbon tetrachloride, 1,2-dichloroethane, chlorobenzene and dichlorobenzene; ethers such as diethyl ether, methyl ethyl ether, diisopropyl ether, dibutyl ether, dioxane, dimethoxyethane (DME), tetrahydrofuran (THF) and diethyleneglycol dimethyl ether (DGM); nitriles such as acetonitrile and propionitrile; bases such as pyridine; and others.

The process (a) is carried out usually in the presence of acid binding agents such as inorganic bases such as hydroxides, carbonates and bicarbonates of alkali metals including sodium hydrogen carbonate, potassium hydrogen carbonate, sodium carbonate, potassium carbonate, lithium hydroxide, sodium hydroxide, potassium hydroxide and calcium hydroxide; inorganic alkali metal amides including lithium amide, sodium amide, potassium amide and the like; and organic bases such as alcoholate, tertiary amines, dialkylaminoanilines and pyridines such as triethylamine, 1,1,4,4-tetramethyl ethylenediamine (TMEDA), N,N-dimethyl-aniline, N,N-diethylaniline, pyridine, 4-dimethylaminopyridine (DMAP), 1,4-diazabi-cyclo[2,2,2]octane (DABCO), 1,8-diazabicyclo[5,4,0]undec-7-ene (DBU), and the like.

Further, the process (a) can be carried out in the presence of catalysts such as by 4-dimethylaminopyridine (DMAP).

In the process (a), the reaction temperature can be varied within a substantially wide range. In general, the reaction is carry out at a temperature of from about 0° C. to about 150° C., preferably about 25° C. to about 100° C.

Also, the reactions can be carried out under atmospheric pressure but may also be under an elevated or reduced pressure.

In carrying out the process (a) according to the invention, the desired compound of the formula (I) can be obtained by reacting about 1 to 1.5 moles of the compound of formula (III) in a diluent such as acetonitorile with 1 mole of the compound of formula (II) in the presence of acid binder, for example, in the presence of 1 to 1.5 moles of 4-dimethylaminopyridine.

In case of using an acid binding agent other than 4-dimethylaminopyridine in these reactions, it is usually preferable to use a catalytic amount of, e.g., 0.03 molar amount to 0.1 molar amount of 4-dimethylaminopyridine in order to selectively obtain the compound of formula (I).

In the above process (b) is usually conducted in the presence of catalysts and the catalysts useful in such cases are exemplified by boron trifluoride ethyl etherate, aluminum chloride, diethylaluminum chloride, and the like.

In the process (b), the reaction temperature can be varied within a substantially wide range. In general, the reaction is carry out at a temperature of from about 0° C. to about 200° C., preferably about 50° C. to about 150° C.

Also, the reaction can be carried out under atmospheric pressure but may also be carryed out under an elevated or reduced pressure.

In carrying out the process (b) according to the invention, the desired compound of the formula (II) can be obtained by reacting about 1 to 1.5 moles of trimethylsilyl azide with 1 mole of the compound of formula (IV) in the presence of catalyst, for example, a catalytic amount of boron trifluoride ethyl etherate.

In the prosesses (b) and (d), after reaction is completed, protic solvents are added, and the protic solvents in this case are exemplified by water, methanol, ethanol, n-propanol, isopropanol, and acetic acid, preferably, methanol.

As appropriate diluents for carrying out the process (c) according to the invention there may be mentioned any kind of inert solvents.

Examples of such diluents are exemplified by acid amides such as N,N-dimethylformamide (DMF), N,N-dimethylaceto-amide (DMA), N-methylpyrrolidone, 1,3-dimethyl-2-imidazolidinone, hexamethyl phosphoric triamide (HMPA); sulfone, sulfoxides such as dimethylsulfoxide (DMSO), sulfolane, and the like.

In the process (c) is usually carried out in the presence of catalysts, exemplified by aluminum chloride, boron trichloride, diethylaluminum chloride, and the like.

In the process (c), the reaction temperature can be varied within a substantially wide range. In general, the reaction is carry out at a temperature of from about 0° C. to about 200° C., preferably about 20° C. to about 150° C.

The reactions can be carried out under atmospheric pressure but may also be carryed out under an elevated or reduced pressure.

In carrying out the process (c) according to the invention, the desired compound of the formula (II) can be obtained by reacting about 1 to 1.5 moles of sodium azide with 1 mole of the compound of formula (IV) in the presence of catalyst, for example, 0.01 to 1 mole of aluminum chloride.

In the process (d), the reaction temperature can be varied within a substantially wide range. In general, the reaction is carry out at a temperature of from about 0° C. to about 200° C., preferably about 25° C. to about 130° C.

The reactions can be carried out under atmospheric pressure but may also be carryed out under an elevated or reduced pressure.

In carrying out the process (d) according to the invention, the desired compound of the formula (II) can be obtained by reacting about 2.5 to 4 moles of trimethylsilyl azide with 1 mole of the compound of formula (V).

As appropriate diluents for carrying out the process (e) according to the invention there may be mentioned any kind of inert solvents.

Examples of such diluents are water; acid amides such as dimethylformamide (DMF), dimethyl acetoamide (DMA), N-methylpyrrolidone, 1,3-dimethyl-2-imidazolidinone, hexamethyl phosphoric triamide (HMPA); sulphoxides such as dimethyl sulfoxide (DMSO), sulfolane, and the like.

In the above process (e) is carried out preferably in the presence of catalysts and the catalyst is exemplified by aluminum chloride.

In the above-mentioned process (e), the reaction temperature can be varied within a substantially wide range. In general, the reaction is carried out at a temperature of from about −30° C. and about 50° C., preferably from 0° C. to 30° C.

The reactions can be carried out under atmospheric pressure but may also be optionally operated under an elevated or reduced pressure.

In carrying out the process (e) according to the invention, the desired compound of the formula (II) can be obtained by reacting about 1 to 1.3 moles of sodium azide in a diluent with 1 mole of the compound of formula (V)in the presence of 1 to 1.2 moles of aluminum chloride.

As appropriate diluents for carrying out the process (f) according to the invention there may be mentioned any kind of inert solvents.

Examples of such diluents are water; alcohols such as methanol, ethanol, isopropanol, butanol and ethyleneglycol, and others.

The above mentioned process (f) is carried out preferably in the presence of acid binding agents, and as examples of such acid binding agents there may be mentioned inorganic bases including hydroxides, carbonates and bicarbonates of alkali metals such as sodium hydrogen carbonate, potassium hydrogen carbonate, sodium carbonate, potassium carbonate, lithium hydroxide, sodium hydroxide, potassium hydroxide, calcium hydroxide, and the like.

In the above-mentioned process (f), the reaction temperature can be varied within a substantially wide range. In general, the reaction is carried out at a temperature of from about −30° C. and about 50° C., preferably from 0° C. to 30° C.

The reactions can be carried out under atmospheric pressure but may also be carryed out under an elevated or reduced pressure.

In carrying out the process (f) according to the invention, the desired compound of the formula (II) can be obtained by reacting about 1 to 1.3 moles of the compound of formula (VIII) in a diluent with 1 mole of the compound of formula (VII)in the presence of 1 to 1.2 moles of acid binding agent.

The tetrazolinone derivatives according to the invention can be used as defoliants, desiccants, agents for destroying broad-leaved plants and, especially, as weedkillers.

By weeds, in the broadest sense, there are to be understood all plants which grow in locations where they are undesired. Whether the substances according to the invention act as total or selective herbicides depends essentially on the amount used.

The tetrazolinone derivatives according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale. Sorghum, Panicum, Saccharum, Ananas, Asparagus and Allium.

However, the use of the tetrazolinone derivatives according to the invention is in no way restricted to these genera, but also extends in the same manner to other plants.

The tetrazolinone derivatives according to the invention are suitable, depending on the concentration, for the total combating of weeds, for example on industrial terrain and rail tracks, and on paths and squares with or without tree plantings. Equally, the tetrazolinone derivatives according to the invention can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The tetrazolinone derivatives according to the invention can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the tetrazolinone derivatives according to the invention with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethyl-sulphoxide.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dye stuffs, azo dye stuffs or metal phthalocyanine dye stuffs, and trace nutrients, such as salts of iron, manganese boron, copper, cobalt, molybdenum and zinc.

The formulations in general contain from 0.1 to 95 per cent by weight of tetrazolinone derivatives according to the invention, preferably from 0.5 to 90 per cent by weight.

The tetrazolinone derivatives according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The tetrazolinone derivatives according to the invention can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The tetrazolinone derivatives according to the invention can be applied either before or after emergence of the plants.

They can also be incorporated into the soil before sowing. They are used, in particular, after emergence of the plants.

The amount of tetrazolinone derivatives according to the incention used can vary within a substantial range. It depends essentially on the nature of the desired effect. In general, the amounts used are between 0.001 and 10 kg of tetrazolinone derivatives according to the invention per hectare of soil surface, preferably between 0.01 and 5 kg per ha.

EXAMPLES

The preparation and use of the tetrazolinone derivatives according to the invention can be seen from the following examples.

Synthesis Example 1

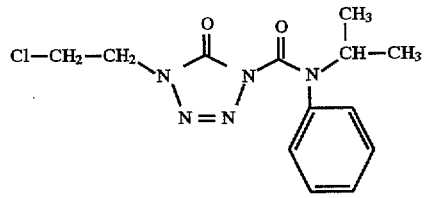

1-(2-Chloroethyl)-5(4H)-tetrazolinone (2 g), DMAP (1.97 g) and N-isopropyl-N-phenyl-carbamoyl chloride (3.17 g) were dissolved in acetonitrile (30 ml), then reacted for 6 hours by heating with refluxing. After distilling off the solvent under reduced pressure, chloroform (30 ml) was added to the residue and was washed with water (20 ml×2).

The chloroform layer was dried over anhydrous sodium sulfate. Then, the solvent was distilled off under reduced pressure, and the residue was subjected to flash column chromatography (hexane:ethyl acetate=5:2) to give 1-(2-chloroethyl)-4-(N-isopropyl-N-phenyl carbamoyl)-5(4H)-tetrazolinone (3.22 g). $n_D^{20}$ 1.5329

Synthesis Example 2

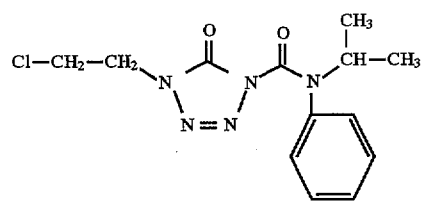

1-(2-Chloroethyl)-5(4H)-tetrazolinone (2 g), DMAP (82 mg), potassium carbonate (2.23 g) and N-isopropyl-N-phenyl-carbamoyl chloride (9.17 g) were suspended in toluene (40 ml) and heated for 17 hours at 60°–65° C. This material was washed with water (20 ml×2) and dried over anhydrous sodium sulfate, followed by distillation off of the solvent and the residue was subjected to flash column chromatography (hexane:ethyl acetate=5:2) giving 1-(2-chloroethyl)-4-N-isopropyl-N-phenylcarbamoyl)-5(4H)-tetrazolinone (3.9 g). $n_D^{20}$ 1.5329

The tetrazolinone derivatives synthesized by foregoing Synthesis Example 1 or Synthesis Example 2 are shown in Table 3 and 4 together with other compounds producible by those processes:

TABLE 3

| Compound No. | $R^1$ | $R^2$ | $R^3$ | Physical constant |
|---|---|---|---|---|
| 1 | ClCH$_2$CH$_2$ | ethyl | ethyl | $n_D^{20}$ 1.5013 |
| 2 | ClCH$_2$CH$_2$ | ethyl | cyclohexyl | $n_D^{20}$ 1.5063 |
| 3 | ClCH$_2$CH$_2$ | n-propyl | n-propyl | $n_D^{20}$ 1.4929 |
| 4 | ClCH$_2$CH$_2$ | allyl | allyl | $n_D^{20}$ 1.5152 |
| 5 | ClCH$_2$CH$_2$ | propargyl | propargyl | $n_D^{20}$ 1.5255 |
| 6 | ClCH$_2$CH$_2$ | methyl | phenyl | $n_D^{20}$ 1.5517 |
| 7 | ClCH$_2$CH$_2$ | ethyl | phenyl | mp 78–79° C. |
| 8 | ClCH$_2$CH$_2$ | n-propyl | phenyl | mp 56–58° C. |
| 9 | ClCH$_2$CH$_2$ | isopropyl | phenyl | $n_D^{20}$ 1.5329 |
| 10 | ClCH$_2$CH$_2$ | n-butyl | phenyl | mp 61.5–63° C. |
| 11 | ClCH$_2$CH$_2$ | phenyl | phenyl | mp 118–119° C. |
| 12 | ClCH$_2$CH$_2$ | isopropyl | 2-fluorophenyl | $n_D^{20}$ 1.5293 |
| 13 | ClCH$_2$CH$_2$ | isopropyl | 3-fluorophenyl | $n_D^{20}$ 1.5239 |
| 14 | ClCH$_2$CH$_2$ | isopropyl | 4-fluorophenyl | $n_D^{20}$ 1.5221 |
| 15 | ClCH$_2$CH$_2$ | isopropyl | 2-methylphenyl | $n_D^{20}$ 1.5293 |
| 16 | ClCH$_2$CH$_2$ | isopropyl | 3-methylphenyl | $n_D^{20}$ 1.5287 |
| 17 | ClCH$_2$CH$_2$ | isopropyl | 4-methylphenyl | mp 46.5–58° C. |
| 18 | ClCH$_2$CH$_2$ | isopropyl | 2-methylthiophenyl | $n_D^{20}$ 1.5523 |
| 19 | CF$_3$CH$_2$ | ethyl | cyclohexyl | $n_D^{20}$ 1.4670 |
| 20 | CF$_3$CH$_2$ | isopropyl | phenyl | mp 117–118° C. |
| 21 | ClCH$_2$CH$_2$CH$_2$ | isopropyl | phenyl | $n_D^{20}$ 1.5315 |
| 22 | ClCH$_2$CH$_2$ | isopropyl | 2-methoxyphenyl | mp 104.5–106° C. |
| 23 | BrCH$_2$CH$_2$ | isopropyl | phenyl | $n_D^{20}$ 1.5418 |

TABLE 3-continued

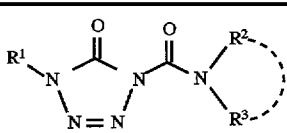

| Compound No. | R¹ | R² | R³ | Physical constant |
|---|---|---|---|---|
| 24 | $CH_3CHCl$ | isopropyl | phenyl | $n_D^{20}$ 1.5335 |
| 25 | $CF_3CH_2$ | isopropyl | 3-methylphenyl | mp 99–101° C. |
| 26 | $CF_3CH_2$ | isopropyl | 4-chlorophenyl | mp 62.5–65° C. |
| 27 | $CF_3CH_2$ | isopropyl | 3-chlorophenyl | mp 83.5–86° C. |
| 28 | $CF_3CH_2$ | isopropyl | 4-methylphenyl | mp 69.5–71° C. |
| 29 | $CF_3CH_2$ | isopropyl | 4-fluorophenyl | mp 88.5–90° C. |
| 30 | $ClCH_2CHCl$ | isopropyl | phenyl | $n_D^{20}$ 1.5374 |

TABLE 4

(in the case where R² and R³ form a heterocyclic ring together with the nitrogen atom to which are they are bonded)

| Compound No. | | Physical constant |
|---|---|---|
| 31 | 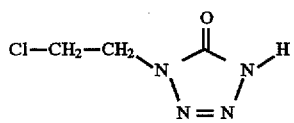 | $n_D^{20}$ 1.5654 |

Synthesis of Intermediate

Synthesis Example 3

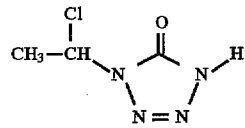

2-chloroethyl isocyanate (10 g), trimethylsilyl azide (16.35 g) and a catalytic amount of boron trifluoride ethyl etherate were mixed and heated for 16 hours with refluxing. The excess trimethylsilyl azide was distilled off under reduced pressure and methanol was added to the residue. Thereafter, methanol was distilled off and the residue was subjected to flash column chromatography (hexane:ethyl acetate=1:1) to give 1(2-chloro-ethyl)-5(4H)-tetrazolinone (11.47 g). mp 79.5°–81.5° C.

Using 3-chloropropyl isocyanate (5 g) instead of 2-chloroethyl isocyanate in Synthesis Example 3, 1-(3-chloropropyl)-5(4H)-tetrazolinone (3.15 g) was obtained. mp 48.5°–53.5° C.

Using chloromethyl isocyanate (5 g) instead of 2-chloroethyl isocyanate in Synthesis Example 3, 1-(chloro-methyl)-5(4H)-tetrazolinone (2.32 g) was obtained. $n_D^{20}$ 1.5091

Synthesis Example 4

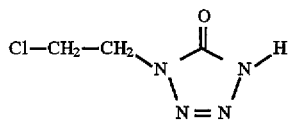

Anhydrous aluminum chloride (0.2 g) was added to a suspension of sodium azide (1.95 g) in anhydrous DMF (18 ml) in an argon stream under ice-cooling and stirred for 15 minutes. Then, 2-chloroethyl isocyanate (3.16 g) was dropped therein and stirring was further continued at 70°–75° C. for 3 hours in an argon stream. After cooling, the reaction mixture was poured into a mixture of sodium nitrite (0.5 g), water (100 ml) and ice (50 g) with stirring and acidified with 10% hydrochloric acid (for coloring of KI-starch paper) and extracted with ethyl acetate. The organic layer was dried over anhydrous sodium sulphate.

Then, the solvent was distilled off under a reduced pressure and the residue was subjected to flash column chromatography (hexane:ethyl acetate=1:1) to give 1-(2-chloroethyl)-5(4H)-tetrazolinone (3.61 g). mp 79.5°–81.5° C.

Synthesis Example 5

2-Chloropropionyl chloride (2 g) and trimethylsilyl azide (6.9 g) were mixed and heated for 16 hours with refluxing. The excess trimethylsilyl azide was distilled off under reduced pressure and methanol was added to the residue. Thereafter, methanol was distilled off and the residue was subjected to flash column chromatography (hexane:ethyl acetate=1:1) to give 1-(1-chloroethyl)-5(4H)-tetrazolinone (1.07 g). $n_D^{20}$ 1.5058

Using 3-bromopropionyl chloride (3.43 g) instead of 2-chloropropionyl chloride (2 g), 1-(2-bromoethyl)-5(4H)-tetrazolinone (3.45 g) was obtained by the similar to that in Synthesis Example 5. mp 69.5°–73.5° C.

Using 2,3-dichloropropionyl chloride (3.23 g) instead of 2-chloropropionyl chloride (2 g), 1-(1,2-dichloroethyl)-5 (4H)-tetrazolinone (1.1 g) was obtained by the process similar to that in Synthesis Example 5. $n_D^{20}$ 1.5058

Synthesis Example 6

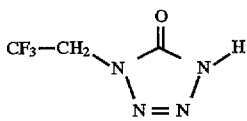

Sodium hydroxide (93%, 2.15 g) was dissolved in 10 ml of water and 1-(2,2,2-trifluoroethyl)-5-mercaptotetrazole (8.29 g) was added thereto to give a homogeneous solution. This solution was diluted with ethanol (60 ml). After cooling to 0° C., propylene oxide (3.40 g) was added dropwise while maintaining the temperature. After stirring at 0° C. for 30 minutes and then at room temperature for 2 hours, the solvent was distilled off under reduced pressure. Water (80 ml) was added to the residue and the insoluble oily matter was removed by washing with ethyl acetate. The aqueous layer was separated and acidified by hydrochloric acid followed by evaporation to dryness under reduced pressure. The residue was extracted with warm ethyl acetate and filtered. The solvent was evaporated under reduced pressure to give 1-(2,2,2-trifluoroethyl)-5(4H)-tetrazolinone (6.58 g). mp 98°–100° C.

Synthesis Example 7

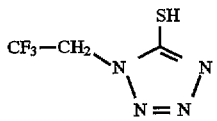

Methyl {N-(2,2,2-trifluoroethyl)}dithio carbamate (11.65 g) and sodium azide (4.95 g) were suspended in 80 ml of water and heated for 30 minutes with refluxing. After cooling, the reaction solution was washed with ethyl acetate and acidified with 10% hydrochloric acid for precipitation. After separation by filtration, the precipitation was dried under a reduced pressure to give 1-(2,2,2-trifluoroethyl)-5-mercapto-tetrazole (10.32 g). mp 122°–124° C.

Biological Test Examples

Test Example 1

Test of pre-emergence soil treatment test
Preparing method carrier: acetone 5 parts by weight
    emulsifier: benzyloxy polyglycol ether 1 part by weight One part by weight of the active compound and the above amounts of a carrier and an emulsifier are mixed to give an emulsion. A prescribed amount of this emulsion is diluted with water to be subjected to the undermentioned tests.

Testing method

In the greenhouse, seeds of *Echinochloa* and *Amaranthus lividus* were sowed in the surface layer of plowed land soil filled in a 120 cm² pot with soil-covering and a prescribed amount of the above tested chemical was uniformly sprayed on the surface layer of soil in the testing pot.

The herbicidal effect was examined after 4 weeks from application.

The herbicidal effect was rated as 100% in the case of complete death and as 0% in the case where equivalent growth was observed to the case without treatment.

Result

The tetrazolinone derivatives of Compounds Nos. 1, 2, 3, 4, 7, 8, 9, 12, 13, 14, 15, 16, 17, 19, 20, 21, 24, and 25 exhibited 100% herbicidal effect against *Echinochloa* and *Amaranthus lividus* by application of 1 kg/ha of the amount.

Test Example 2

Test of post-emergency foliage treatment
Testing method

In the greenhouse, seeds of *Echinochloa* and *Amaranthus lividus* were sowed each in a 120 cm² pot filled with plowed land soil and covered with soil. After 10 days from sowing and soil-covering (when the weeds on average were in two-leaf stage), a prescribed amount of the chemical prepared similarly to those in above Test Example 1 was uniformly spread on the foliage part of each test plant in the testing pot. After 3 weeks from spreading, the herbicidal effect was examined.

Result

In this test, the tetrazolinone derivatives of Compounds Nos. 1, 2, 3, 4, 7, 8, 9, 13, 14 and 20 exhibited a herbcidal effect of 90% or more against *Echinochloa* and 80% or more against *Amaranthus lividus* by application of 2.0 kg/ha of the amount.

Formulation Example 1 (granules)

Water (25 parts) is added to a mixture of Compound No. 3 (10 parts), bentonite (montmorillonite) (30 parts), talc (58 parts) and lignin sulphonate salt (2 parts) with kneading and formed into 10–40 mesh granules using an extrusion-type granulator followed by drying at 40°–50° C.

Formulation Example 2 (granules)

A clay mineral (95 parts) having a particle size distribution of 0.2–2 mm is introduced in a rotary mixer and Compound No. 8 is sprayed therein with a liquid diluent under rotation to wet uniformly, followed by drying at 40°–50° C.

Formulation Example 3 (emulsion)

An emulsion is obtained by mixing Compound No. 20 (30 parts), xylene (5 parts), polyoxyethylene alkyl phenyl ether (8 parts) and calcium alkylbenzene sulphonate (7 parts) with stirring.

Formulation Example 4 (wettable powder)

A wettable powder is prepared by mixing Compound No. 1 (15 parts), a mixture (1:1) of White Carbon (fine powder of hydrated non-crystalline silicon oxide) (80 parts) and powdery clay, sodium alkylbenzene sulphonate (2 parts) and a condensate of sodium alkylnaphthalene sulphonate and formaldehyde (3 parts) in a powdery state.

Formulation Example 5 (wettable granules)

Wettable granules are prepared by thoroughly mixing Compound No. 2 (20 parts), sodium lignin sulphonate (30 parts), bentonite (15 parts) and calcined diatomaceous earth powder (35 parts) followed by addition of water and extrusion through a 0.3 mm screen and drying.

It will be understood that the specification and examples are illustrative but not limitative to the present invention and that other embodiments within the spirit and scope of the invention will suggest themselves to those skill in the art.

We claim:

1. A tetrazolinone derivative of the formula:

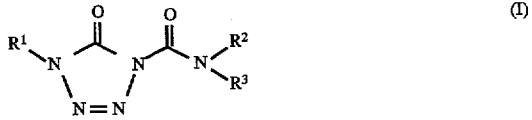

(I)

wherein
    $R^1$ is alkyl substituted by halogen, and
    $R^2$ and $R^3$ each independently is alkyl, alkenyl, alkynyl, cycloalkyl which may optionally be substituted, phenyl or substituted phenyl, or $R^2$ and $R^3$ together with the N-atom to which they are attached, are a 5- or 6-membered heterocyclic ring which may optionally be substituted.

2. A tetrazolinone derivative according to claim 1, wherein $R^1$ is $C_{1-6}$ alkyl which is substituted by one or more of fluorine, chlorine or bromine, and $R^2$ and $R^3$ each independently is $C_{1-6}$ alkyl, $C_{2-6}$ alkenyl, $C_{3-6}$ alkynyl, $c_{3-8}$ cycloalkyl which may optionally be substituted by $C_{1-6}$ alkyl, or phenyl or phenyl having at least one substituent selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ alkylthio and $C_{1-4}$ haloalkylthio, or $R^2$ and $R^3$ together with the N-atom to which they are attached, are a 5- or 6-membered saturated heterocyclic ring optionally substituted by alkyl and/or condensed with a hydrocarbon ring.

3. A tetrazolinone derivative according to claim 1, wherein $R^1$ is $C_{1-3}$ alkyl which is substituted by one or more of fluorine, chlorine or bromine, and $R^2$ and $R^3$ each independently is $C_{1-4}$ alkyl, cyclopropyl which may optionally be substituted by methyl, cyclopentyl which may optionally be substituted by methyl, cyclohexyl which may optionally be substituted by methyl, allyl, propargyl, phenyl, or phenyl having at least one substituent selected from the group consisting of fluorine, chlorine, bromine, methyl, ethyl, methoxy, methylthio, nitro, cyano, trifluoromethyl, trifluoromethoxy, difluoromethoxy, 2,2,2-trifluoroethoxy, trifluoromethylthio and 2,2,2-trifluoroethylthio, or $R^2$ and $R^3$ together with the N-atom to which they are attached, are piperidino, methylpiperidino, morpholino, indol-1-yl, perhydroindol-1-yl, 1,2,3,4-tetrahydroquinolin-1-yl, 2-methyl-1,2,3,4-tetrahydroquinolin-1-yl, or perhydroquinolin-1-yl.

4. A herbicidal composition comprising a herbicidally effective amount of a compound according to claim 1 and a diluent.

5. A method of combating unwanted vegetation which comprises applying to such vegetation or to a locus from which it is desired to exclude such vegetation a herbicidal effective amount of a compound according to claim 1.

6. A compound of the formula:

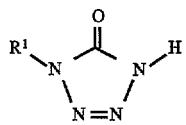

(II)

wherein $R^1$ is alkyl substituted by halogen.

7. A compound according to claim 6, in which $R^1$ is $C_{1-6}$ alkyl which is substituted by one or more of fluorine, chlorine or bromine.

8. A compound according to claim 6, in which $R^1$ is $C_{1-3}$ alkyl which is substituted by one or more of fluorine, chlorine or bromine.

9. A tetrazolinone derivative of the formula:

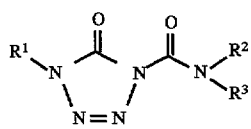

(I)

wherein $R^1$ is $C_{1-6}$-alkyl which is substituted by one or more of fluorine, chlorine or bromine; and $R^2$ and $R^3$ each independently is $C_{1-6}$-alkyl, $C_{2-6}$-alkenyl, $C_{3-6}$-alkynyl, $C_{3-8}$-cycloalkyl which may optionally be substituted by $C_{1-6}$-alkyl, or phenyl or phenyl having at least one substituent selected from the group consisting of halogen, cyano, nitro, $C_{1-4}$-alkyl, $C_{1-4}$-haloalkyl, $C_{1-4}$-alkoxy, $C_{1-4}$-haloalkoxy, $C_{1-4}$-alkylthio and $C_{1-4}$-haloalkylthio; or $R^2$ and $R^3$ together with the N-atom to which they are bonded, form piperidino, methylpiperidino, morpholino, indol-1-yl, perhydroindol-1-yl, 1,2,3,4-tetrahydroquinolin-1-yl, 2-methyl-1,2,3,4-tetrahydroquinolin1yl, or perhydroquinolin-1-yl.

10. A herbicidal composition comprising a herbicidally effective amount of a compound according to claim 9 and a diluent.

11. A method of combating unwanted vegetation which comprises applying to such vegetation or to a locus from which it is desired to exclude such vegetation a herbicidally effective amount of a compound according to claim 9.

* * * * *